United States Patent [19]

Allen

[11] Patent Number: 5,346,459
[45] Date of Patent: Sep. 13, 1994

[54] TROCAR

[75] Inventor: John J. Allen, Mendota Heights, Minn.

[73] Assignee: Minnesota Mining and Manufacturing Company, St. Paul, Minn.

[21] Appl. No.: 48,274

[22] Filed: Apr. 14, 1993

[51] Int. Cl.$^5$ .............................................. A61B 17/34
[52] U.S. Cl. ................................... 606/185; 604/164
[58] Field of Search .................. 606/185; 604/165, 164

[56] References Cited

U.S. PATENT DOCUMENTS

| | | | |
|---|---|---|---|
| 1,527,291 | 2/1925 | Zorraquin . | |
| 2,630,803 | 3/1953 | Baran . | |
| 3,713,447 | 1/1973 | Adair | 128/347 |
| 3,774,604 | 11/1973 | Danielsson | 128/214.4 |
| 4,190,048 | 2/1980 | Sampson | 128/215 |
| 4,403,617 | 9/1983 | Tretiayak | 128/754 |
| 4,431,426 | 2/1984 | Groshong et al. | 604/280 |
| 4,535,773 | 8/1985 | Yoon | 604/51 |
| 4,601,710 | 7/1986 | Moll | 604/165 |
| 4,617,929 | 10/1986 | Gill | 128/305 |
| 4,617,933 | 10/1986 | Hasson | 128/348 |
| 4,654,030 | 3/1987 | Moll et al. | 604/165 |
| 4,747,831 | 5/1988 | Kulli | 604/110 |
| 4,808,168 | 2/1989 | Warring | 604/158 |
| 4,813,426 | 3/1989 | Haber et al. | 128/763 |
| 4,902,280 | 2/1990 | Lander | 604/165 |
| 4,906,236 | 3/1990 | Alberts et al. | 604/198 |
| 4,922,602 | 5/1990 | Mehl | 29/460 |
| 4,931,042 | 6/1990 | Holmes et al. | 604/164 |
| 4,943,280 | 7/1990 | Lander | 604/169 |
| 4,952,207 | 8/1990 | Lemieux | 604/164 |
| 4,955,870 | 9/1990 | Ridderheim et al. | 604/195 |
| 5,030,206 | 7/1991 | Lander | 604/164 |
| 5,066,288 | 11/1991 | Deniega et al. | 604/274 |
| 5,104,382 | 4/1992 | Brinkerhoff et al. | 604/165 |
| 5,104,383 | 4/1992 | Shichman et al. | 604/167 |
| 5,114,407 | 5/1992 | Burbank | 604/164 |
| 5,116,353 | 5/1992 | Green | 604/164 X |
| 5,122,122 | 6/1992 | Allgood | 604/174 |
| 5,129,885 | 7/1992 | Green et al. | 604/164 |
| 5,152,754 | 10/1992 | Plyley et al. | 604/164 |
| 5,158,522 | 10/1992 | Borgia et al. | 604/165 |
| 5,158,552 | 10/1992 | Borgia et al. | 604/165 |
| 5,176,651 | 1/1993 | Allgood et al. | 604/167 |
| 5,217,451 | 6/1993 | Freitas | 606/1 |
| 5,224,930 | 7/1993 | Spaeth et al. | 604/33 |
| 5,224,951 | 7/1993 | Freitas | 606/172 |
| 5,226,426 | 7/1993 | Yoon | 128/753 |
| 5,226,891 | 7/1993 | Bushatz et al. | 604/165 |

FOREIGN PATENT DOCUMENTS

| | | |
|---|---|---|
| 0265193A2 | 4/1988 | European Pat. Off. . |
| 0135364 | 2/1989 | European Pat. Off. . |
| 0479130A1 | 4/1992 | European Pat. Off. . |
| 0494520 | 7/1992 | European Pat. Off. . |
| WO93/04632 | 3/1993 | PCT Int'l Appl. . |
| WO93/04715 | 3/1993 | PCT Int'l Appl. . |
| WO93/04716 | 3/1993 | PCT Int'l Appl. . |
| WO93/04717 | 3/1993 | PCT Int'l Appl. . |
| 897224 | 1/1982 | U.S.S.R. . |
| 921554 | 4/1982 | U.S.S.R. . |
| 878265 | 11/1991 | U.S.S.R. . |

OTHER PUBLICATIONS

A product brochure entitled "Lock In Your Position", by Dexide Inc. (5 pages), 1991.

*Primary Examiner*—Michael H. Thaler
*Attorney, Agent, or Firm*—Gary L. Griswold; Walter N. Kirn; Jeffrey J. Hohenshell

[57] ABSTRACT

A trocar for placement in the lumen of a cannula to facilitate insertion of the cannula through the wall of a body cavity is described. The trocar comprises a handle, an obturator having a proximal portion and a distal portion with a cutting surface for piercing the wall of the body cavity, and an axis. The proximal and distal portions of the obturator are mounted for relative angular movement about the axis of the obturator. A mechanism retracts the obturator proximally relative to the cannula along an axial path as the proximal and distal portions move angularly relative to each other after the cutting surface has at least partially penetrated through the wall of the body cavity. Preferably, the path is free of distal movement of the obturator relative to the cannula.

40 Claims, 13 Drawing Sheets

TROCAR

TECHNICAL FIELD

The present invention is directed to trocars for inserting an access tube through an abdominal wall, and more particularly to a trocar having a retractable obturator.

BACKGROUND

A large number of abdominal surgical procedures are performed with laparoscopic techniques in order to avoid a large skin incision. Typically in laparoscopic surgery, a special needle (e.g. a needle similar to the needles described in U.S. Pat. No. 4,808,168 and U.S. patent application Ser. No. 07/808,152, both of which are herein expressly incorporated by reference) is inserted through the skin, and used to inflate the abdominal cavity with an insufflating gas such as carbon dioxide ($CO_2$). Once the abdomen is adequately dilated, the needle is removed and a rigid access tube or cannula with a diameter larger than the pneumoneedle (for example 5, 10 or 11 mm) is passed through the skin in generally the same location.

The access tube provides access for laparoscopic surgical tools such as a laparoscope, the stapler described in U.S. Pat. No. 5,040,715 or the surgical clip appliers described in U.S. Pat. Nos. 5,084,057 and 5,100,420. To drive the access tube through the skin, the surgeon places a trocar in the lumen of the access tube to provide a sharp leading edge for cutting tissue.

The art is replete with trocar devices, including those shown in U.S. Pat. Nos. 4,535,773, 4,601,710, 4,654,030, 4,902,280 and 4,931,042. Those trocars typically comprise an obturator with cutting surfaces for penetrating the skin, and a spring-loaded protective sleeve that surrounds the obturator. As these trocar devices are urged through the skin, friction with the skin causes the protective sleeve to slide proximally (rearwardly). After the access tube has penetrated through the skin, there is no longer friction between the protective sleeve and the skin, and the spring is designed to urge the protective sleeve distally (forwardly) to cover the cutting surfaces. Some of those trocars lock the protective sleeve in the forward position to reduce the risk of accidental puncture of the underlying organs.

These prior art trocars rely on a similar principle of operation: the friction or drag on the protective sleeve as the trocar is advanced through the skin pushes the protective sleeve back (proximally) to expose the cutting surfaces. Once the access tube has penetrated the skin, the drag on the protective sleeve is reduced and the sleeve accelerates distally (forwardly) under the bias of the spring to cover the cutting surfaces.

Those existing trocars encounter problems because a significant amount of force usually must be applied to penetrate the skin (particularly the tough fascia). As a result of the significant insertion force, the trocar may continue to advance toward the underlying organs after it has penetrated the skin. The protective sleeve must "catch up" to the moving trocar point before the trocar reaches the underlying organs. This action may be delayed if the protective sleeve is hung up on tissue.

In addition to the prior art trocars described above, several documents disclose trocars which ultimately retract the obturator relative to the cannula after the obturator has pierced the tissue of abdominal wall. Such documents include U.S. Pat. Nos. 4,535,773 to Yoon, 5,116,353 to Green (and related European Patent Publication 0 479 130), U.S. Pat. Nos. 5,104,382 to Brinkerhoff et al. and 5,152,754 to Plyley et al. Additionally, a trocar having an obturator which ultimately retracts relative to the cannula has been on sale in this country by Origin Medsystems, Inc. prior to the filing date of the present application.

However, with the trocar sold by Origin Medsystems, Inc. and the trocars described in U.S. Pat. No. 5,116,353 to Green (and related European Patent Publication 0 479 130), the obturator first moves distally away from the cannula (and thus toward the underlying organs) in order to actuate the mechanism which ultimately retracts the obturator relative to the cannula. This distal movement occurs just at the time when it is least desirable, that is, the distal movement of the obturator relative to the cannula occurs when the obturator pierces the tissue of the abdominal wall, clearly an undesirable result.

U.S. Pat. No. 5,152,754 discloses a trocar comprising an obturator which retracts relative to the access tube just after the obturator pierces the tissue defining the body cavity. U.S. Pat. No. 5,104,382 also discloses an obturator which retracts relative to a cannula. However, in each of U.S. Pat. Nos. 5,152,754 and 5,104,382, the devices include a member between the obturator and the cannula which necessarily limits the size of the obturator. For example, Brinkerhoff et al., U.S. Pat. No. 5,104,382, includes a shield between the obturator and cannula.

BRIEF DESCRIPTION OF THE INVENTION

According to the present invention there is provided a trocar which (1) automatically retracts an obturator relative to a cannula after the tissue defining a body cavity has been penetrated; (2) includes a retracting means for retracting the obturator relative to the cannula after the tissue has been penetrated along a path which is at least substantially free of distal movement of the obturator relative to the cannula, and preferably completely free of distal movement of the obturator relative to the cannula; (3) preferably includes the retracting means in a proximal portion of the obturator where it is remote from cutting surfaces of the obturator where it may be adversely affected by tissue, blood, fat, etc.; (4) preferably includes a retracting means which is completely independent of the cannula; (5) is preferably free of structure (e.g. such as a trigger or protective sleeve and its attendant bias which may increase the insertion force of the trocar) between the obturator and the cannula at the distal end of the cannula to afford a smooth transition between the obturator and the cannula at the distal end of the cannula, and to eliminate the chance that such structure (e.g. the trigger or protective sleeve) may damage or traumatize tissue; (6) is preferably free of structure between the cannula and the obturator at the distal end of the cannula so that the size of the obturator for use with a given size cannula may be maximized, and conversely, so that the size of the cannula for use with a given obturator may be minimized; and (7) which uses mechanical force or pressure sensing means to sense when the tissue defining the body cavity has been penetrated so that the trocar does not rely upon any electronic components which introduce response times and the potential for electronic failure which may prevent the proper operation of the trocar.

According to the present invention, there is provided a trocar for facilitating insertion of a cannula through tissue defining a body cavity, such as the abdominal wall of a patient. The trocar comprises a housing, and an obturator extending from the housing.

The obturator comprises a shaft for placement in a lumen of the cannula, and cutting surfaces for cutting the tissue. The obturator is mounted for movement between a tissue cutting position with the cutting surfaces projecting beyond a distal end of the cannula, and a retracted position with the cutting retracted within the distal end of the cannula.

The obturator is elongate and has a longitudinal axis defining axial and radial directions and angular displacements. Preferably the obturator comprises a proximal portion having a pin, and a distal portion having the cutting surfaces. The pin is mounted for angular movement relative to the distal portion of the obturator between an armed position and a release position that is angularly spaced from the armed position relative to the longitudinal axis. The trocar also includes a retracting means for biasing the obturator from the tissue cutting position toward the retracted position.

Additionally, the trocar includes a clutch for retaining the obturator in the tissue cutting position against the bias of the retracting means while the tissue is being cut, and for automatically releasing the obturator to allow the retracting means to retract the obturator from the tissue cutting position toward the retracted position after the trocar has at least partially penetrated the tissue. Alternatively, the clutch may be described as a latching and mechanical sensing and releasing means.

The clutch affords movement of the obturator from the tissue cutting position toward the retracted position along a path that is substantially free of distal movement of the obturator relative to the cannula. More preferably, the path of the obturator after the tissue has been at least partially penetrated is completely free of distal movement of the obturator relative to the cannula.

The retracting means retracts the obturator from the tissue cutting position to the retracted position after the pin moves about the longitudinal axis from the armed position toward the release position. The retracting means comprises an axial biasing means for axially biasing the obturator from the tissue cutting position toward the retracted position, and angular biasing means for biasing the pin toward the release position. Preferably the retracting means comprises a coil spring that provides a torque for angularly moving the pin from the armed toward the release position, and that provides an axial force for moving the obturator toward the retracted position.

The clutch preferably comprises the proximal portion of the obturator having a first, friction clutch surface, and the distal portion of the obturator having a second, friction clutch surface. When the obturator is pressed against the tissue, the second, friction clutch surface frictionally engages the first, friction clutch surface and contributes to a first resistance to angular movement about the longitudinal axis between the proximal and distal portions of the obturator from the armed toward the release position. When the tissue has been at least partially penetrated by the obturator, resistance to angular (e.g. rotational) movement between the proximal and distal portions of the obturator about the longitudinal axis is less than the torque, and the proximal portion of the obturator is allowed to rotate from the armed position toward the release position.

The trocar housing has guide surfaces including a ledge surface that abuts the pin to retain the pin in the armed position prior to the obturator being advanced against the tissue. Preferably, the clutch comprises an arming ring having a shoulder surface that abuts the pin as the obturator is advanced through the tissue to restrict movement of the obturator from the tissue cutting position to the retracted position, and surfaces defining an aperture which are angularly spaced from the shoulder surface and which allow the pin to pass when the obturator moves from the tissue cutting position toward the retracted position.

The arming ring is mounted for axial movement between a distal position and a proximal position. The clutch also preferably comprises arming ring biasing means for providing an arming ring biasing force for biasing the arming ring distally, and retaining means for releasably retaining the arming ring in the proximal position against the bias of the arming ring biasing means. Prior to pressing the obturator against the tissue, the arming ring biasing means biases the obturator distally through abutment between the pin and the shoulder surface of the arming ring, and the abutment between the shoulder surface of the arming ring and the pin resists movement of the obturator to the retracted position. As the obturator is pressed against the tissue, the arming ring moves from the distal position toward the proximal position where the retaining means engages the arming ring to retain the arming ring in the proximal position.

BRIEF DESCRIPTION OF THE DRAWINGS

The present invention will be further described with reference to the accompanying drawing wherein like reference numerals refer to like parts in the several views, and wherein:

FIG. 3A through 6C sequentially illustrate the operation of a trocar according to the present invention wherein:

FIGS. 3A, 3B and 3C illustrate the approximate positions of elements of a trocar according to the present invention with the obturator in a retracted position relative to the cannula; wherein:

FIG. 3A is a perspective view of some of the elements of the trocar according to the present invention, illustrating the position of the elements when the obturator is in a retracted position;

FIG. 3B is a partial side view of the trocar according to the present invention and a portion of a cannula with portions of each omitted to illustrate details, and which illustrates the obturator retracted within the distal end portion of the cannula;

FIG. 3C is a perspective view of portions of the trocar according to the present invention and a cannula with portions of each broken away or omitted to illustrate details, which illustrates many of the elements of the trocar shown in FIG. 3A but which shows a different cutting surface;

FIGS. 4A, 4B and 4C illustrate the approximate positions of elements of a trocar according to the present invention with an obturator in a distalmost position relative to the cannula, such as occurs when a user is pressing on a button member of the present invention after the button member is moved to its distal limit; wherein:

FIG. 4A is a perspective view of some of the elements of the trocar according to the present invention, illustrating the position of the elements when the obturator is in a distalmost position;

FIG. 4B is a partial side view of the trocar according to the present invention and a portion of a cannula with portions of each omitted to illustrate details, and which illustrates the obturator in a distalmost position relative to the cannula;

FIG. 4C is a perspective view of portions of the trocar according to the present invention and a cannula with portions of each broken away or omitted to illustrate details, which illustrates many of the elements of the trocar shown in FIG. 4A but which shows a different shaped cutting surface;

FIGS. 5A and 5B illustrate the approximate positions of elements of a trocar according to the present invention with an obturator in an "armed" position that is spaced slightly proximally relative to the cannula from its position shown in FIGS. 4B and 4C, such as occurs when a user releases pressure on the button member after the button member is moved to the position shown in FIGS. 4A, 4B and 4C, but prior to cutting tissue; wherein:

FIG. 5A is a perspective view of some of the elements of the trocar according to the present invention, illustrating the position of the elements when the obturator in the armed position;

FIG. 5B is a partial side view of the trocar according to the present invention and a portion of a cannula with portions of each omitted to illustrate details, and which illustrates the obturator in a position that is spaced slightly proximally relative to the cannula than its position shown in FIG. 4B;

FIGS. 6A, 6B and 6C illustrate the approximate positions of elements of a trocar according to the present invention with an obturator in an "tissue cutting" or extended position that is spaced slightly proximally relative to the cannula from its position shown in FIG. 5B, such as occurs when a user presses the obturator against tissue, but prior to complete penetration of the tissue; wherein:

FIG. 6A is a perspective view of some of the elements of the trocar according to the present invention, illustrating the position of the elements when the obturator is in a tissue cutting position;

FIG. 6B is a partial side view of the trocar according to the present invention and a portion of a cannula with portions of each omitted to illustrate details, and which illustrates the obturator in a tissue cutting position;

FIG. 6C is a perspective view of portions of the trocar according to the present invention and a cannula with portions of each broken away or omitted to illustrate details, which illustrates many of the elements of the trocar shown in FIG. 6A but which shows a different shaped cutting surface;

FIGS. 7A through 7F are perspective, partially schematic views of portions of a trocar according to the present invention which sequentially illustrate movement of some of the elements of the trocar during use of the trocar; wherein:

FIGS. 7A, 7B, 7C and 7D sequentially show the approximate positions of some of the elements of the trocar as the obturator is moved from its position shown in FIG. 3B to its position shown in FIG. 4B;

FIG. 7E shows the approximate position of some of the elements of the trocar when the obturator is in the position shown in FIG. 5B;

FIG. 7F shows the approximate position of some of the elements of the trocar when the obturator is in the position shown in FIG. 6B;

DETAILED DESCRIPTION

Figure 1:
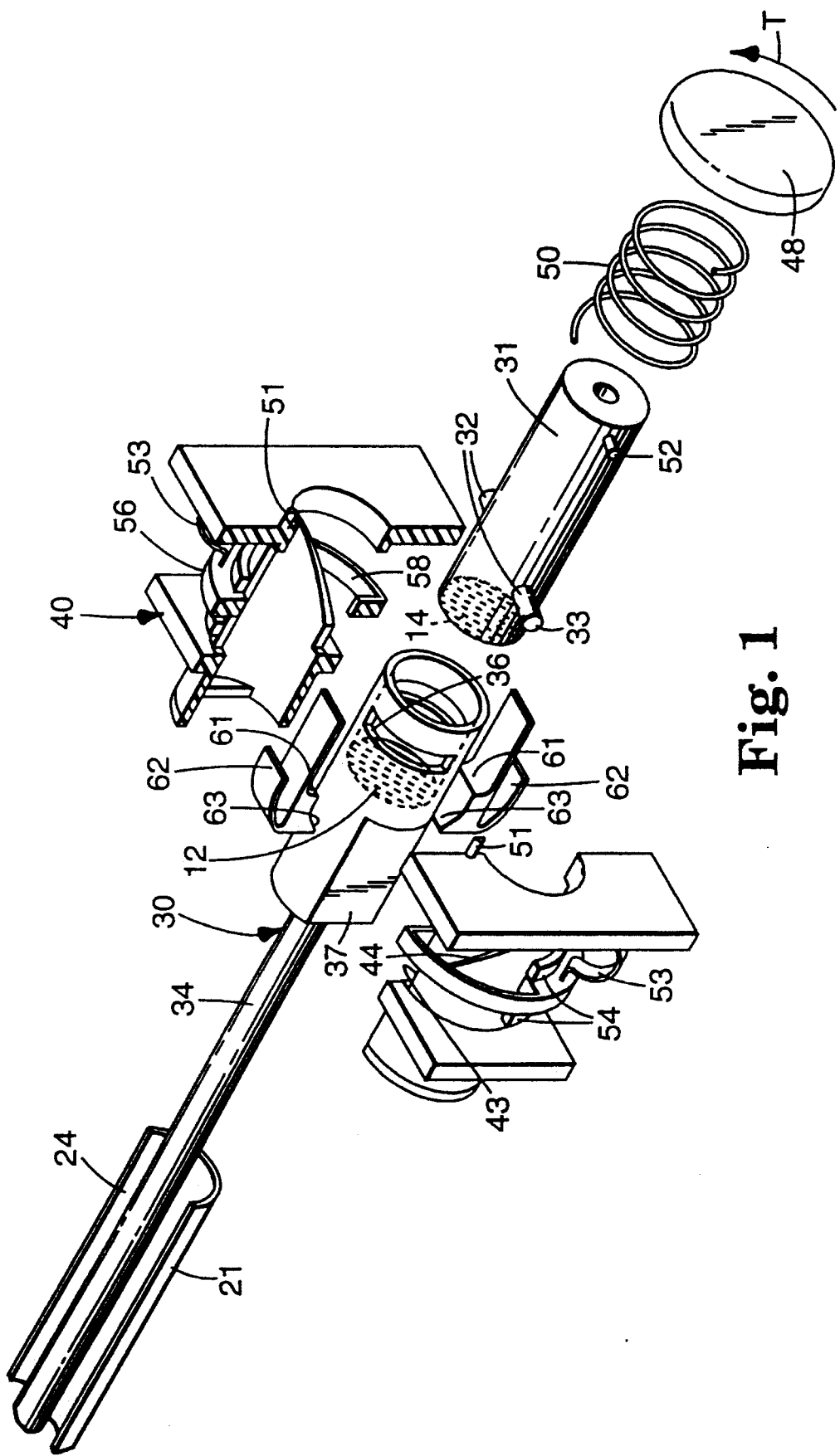
FIG. 1 is an exploded view of portions of a trocar according to the present invention and a portion of a cannula for use with the trocar.

Referring now to FIGS. 1 through 10 of the drawing there is shown an embodiment of a trocar device or assembly generally designated by reference character 10. The trocar 10 is adapted to be placed in a cannula 20 to facilitate the insertion of the cannula 20 through tissue 9 defining a body cavity (see FIG. 2). For example, the tissue 9 may comprise the abdominal wall of a patient and the body cavity may comprise the abdominal cavity of a patient.

The cannula 20 may include an access tube 21 having a lumen 24 terminating in a distal end 22. The cannula 20 is preferably used during laparoscopic surgery and has a large, generally funnel-shaped fixture 26 at its proximal end. The access tube 21 provides an entryway for instruments used in surgery such as laparoscopes, staplers and clip appliers. Examples of such surgical instruments are described in U.S. Pat. Nos. 5,040,715, 5,084,057, 5,100,420, 5,171,247, 5,171,249 and 5,176,695 are herein expressly incorporated by reference.

The cannula 20 may include means for supplying pressurized gas to the abdomen such as a stopcock valve 23. The stopcock valve 23 is a means by which pressurized fluid (insufflating gas) can be provided to the lumen 24 to maintain gas pressure in the body cavity, and thereby keep the cavity inflated to facilitate the surgical procedure.

The cannula 20 may also include a means such as a trap door valve (not shown) generally adjacent the proximal end of the cannula 20 to restrict the escape of fluid through the cannula when it is not occluded by the trocar or surgical instrument. For example, the trap door may comprise a trap door similar to the trap door shown in U.S. Pat. No. 5,152,754, the entire contents of which are herein expressly incorporated by reference. Alternatively, the trap door valve may be replaced with a slotted elastomeric valve similar to the valve shown in U.S. Pat. No. 4,177,814, the entire contents of which is also herein expressly incorporated by reference. Other alternatives may also be utilized to retain pressure within the abdominal cavity when the surgical tool or trocar is removed from the cannula 20, such as an iris-like valve.

The trocar 10 comprises a housing or handle 28 and an elongate obturator 30 extending from the housing 28. The handle 28 is generally rounded to conform to the palm of a user. The handle 28 is adapted to be received in an upper or proximal portion of the cannula 10 which restricts movement of the cannula 20 relative to the housing 28 (see FIG. 2).

Figure 2:
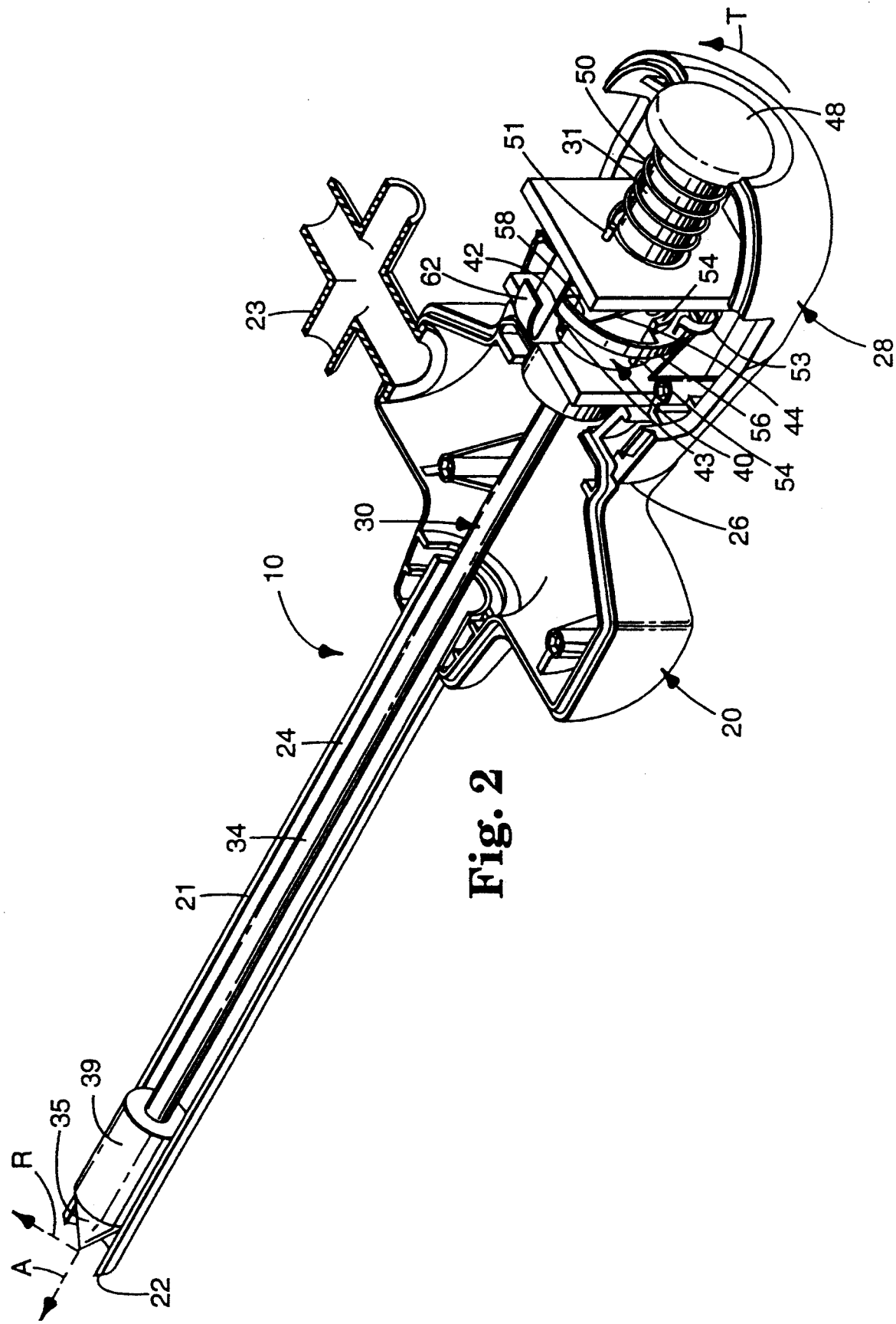
FIG. 2 is a perspective view of a trocar according to the present invention assembled in a cannula with portions broken away or omitted to illustrate details.

The direction of elongation of the obturator 30 and its center define an imaginary, longitudinal axis A (and thus axial directions), and also radial direction R (FIG. 2). Angular displacements may also be measured relative to the axis A of the trocar.

The obturator 30 comprises a proximal portion 31 having a locking pin 32, and a distal portion having a shaft 34 for placement in the lumen 24 of the cannula 20, pin slot surfaces 36 for receiving the pin 32, and cutting surfaces 35 for cutting the tissue 9.

Figure 3A:
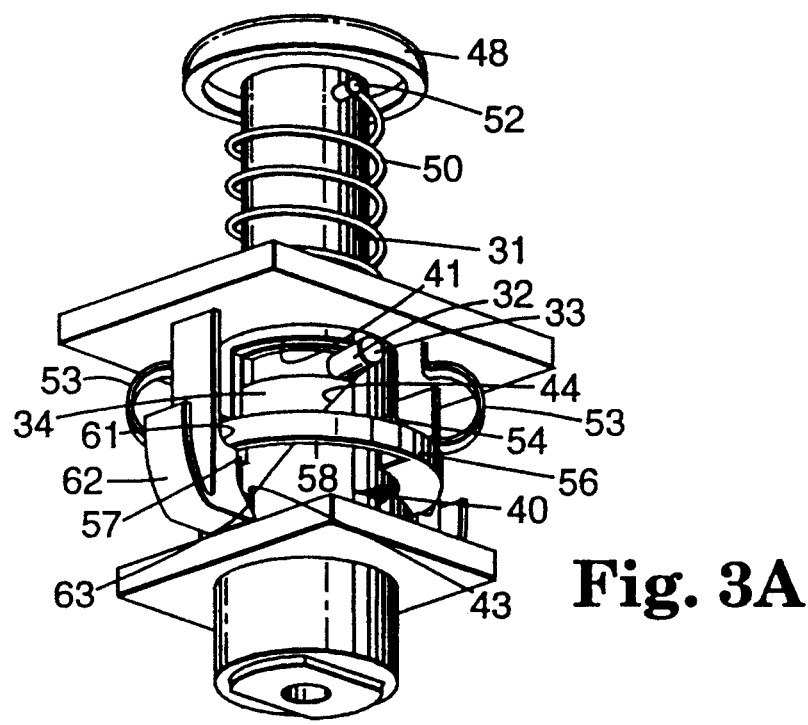
Figure 3B:
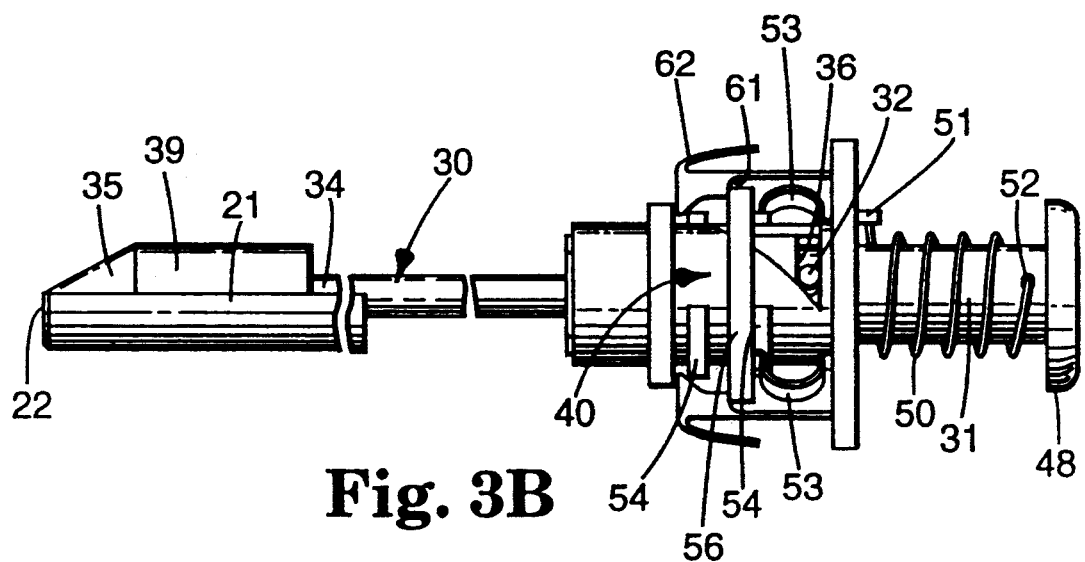
Figure 3C:
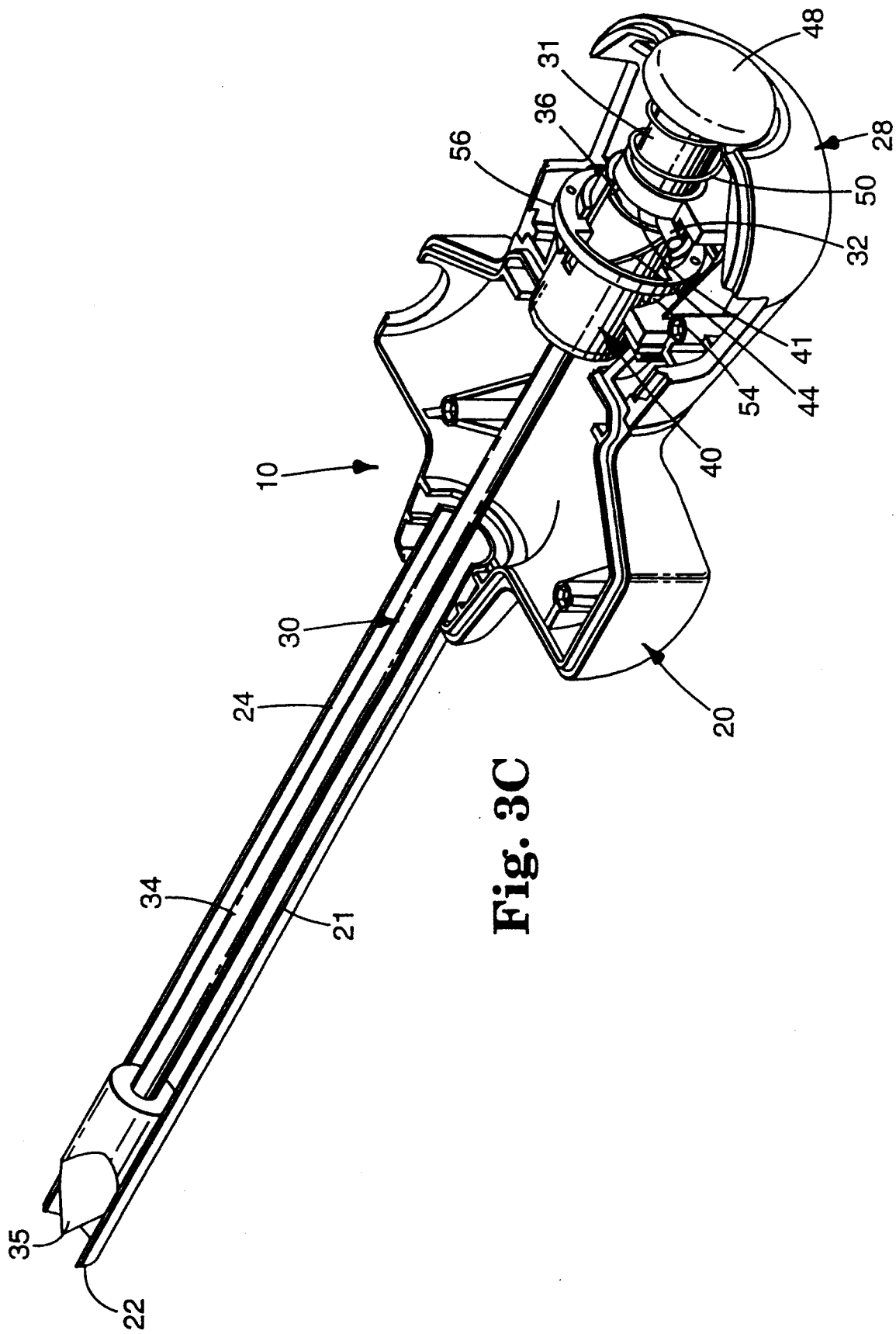
Figure 4A:
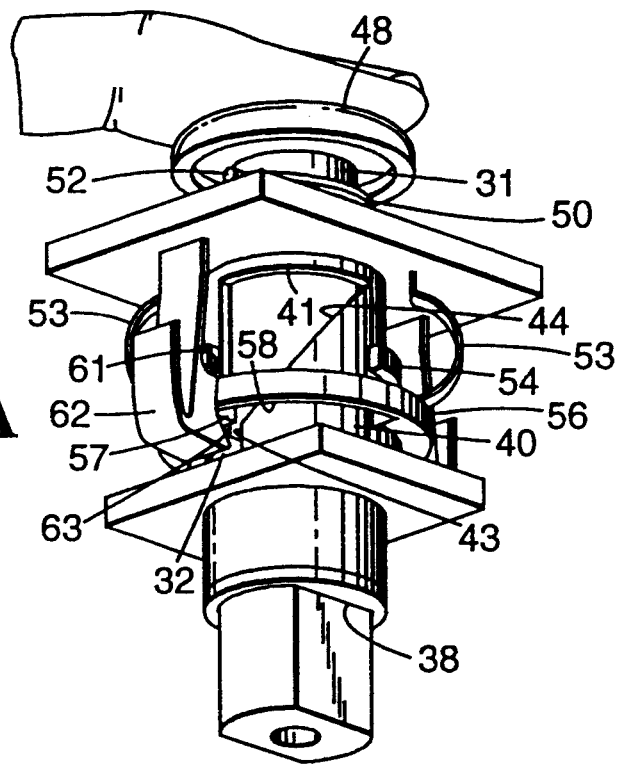
Figure 4B:
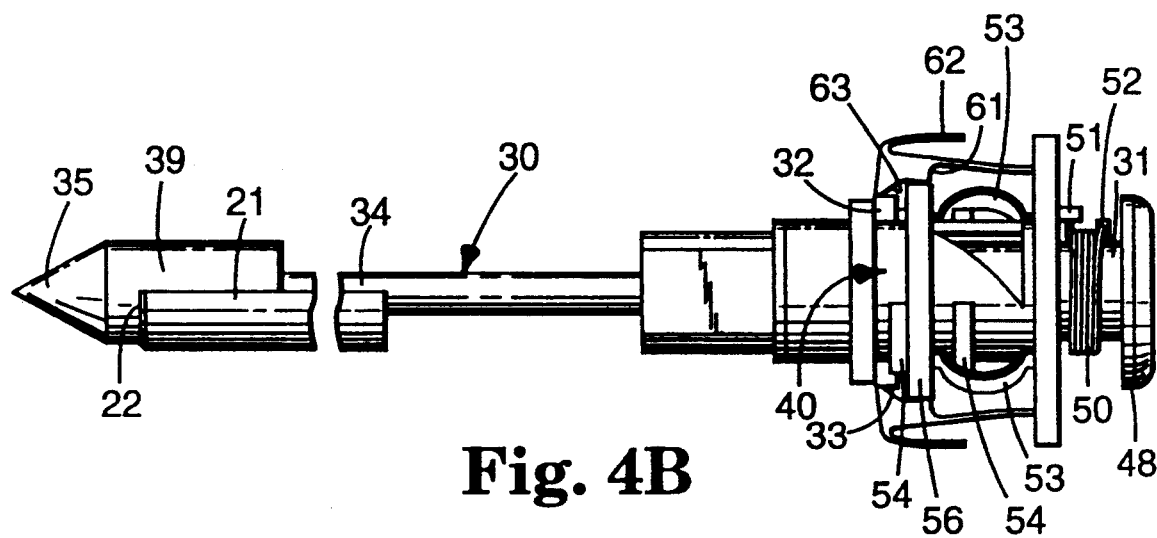
Figure 4C:
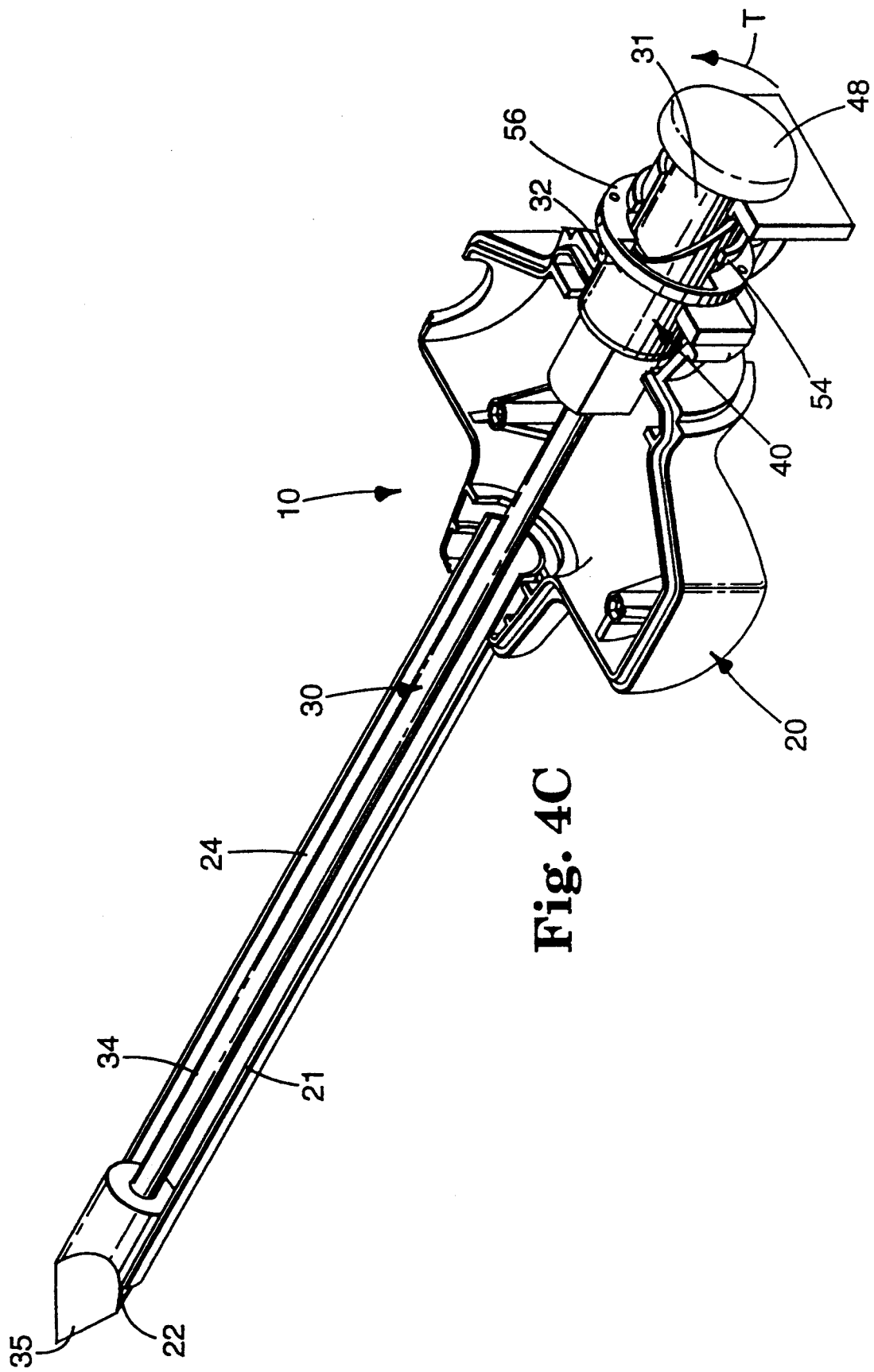
Figure 5A:
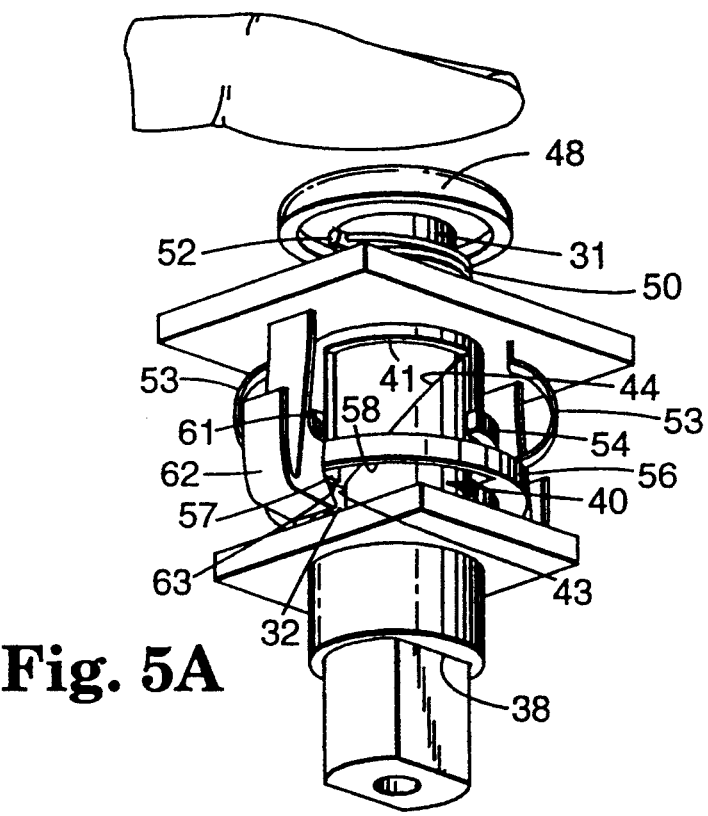
Figure 5B:
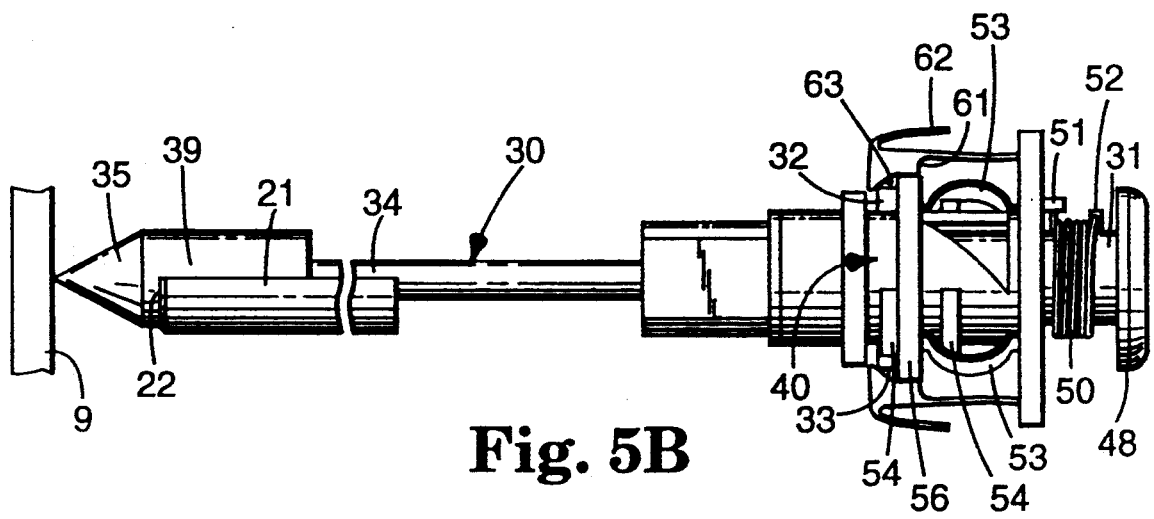
Figure 6A:
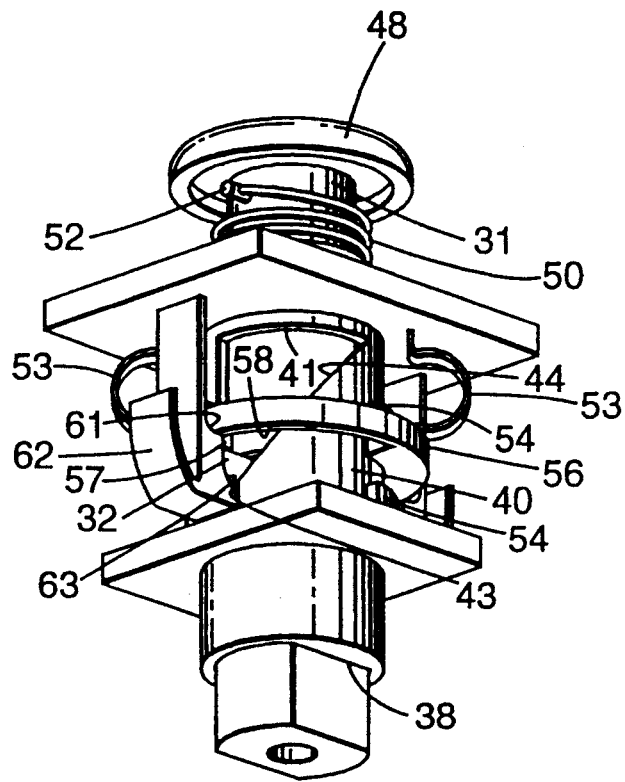
Figure 6B:
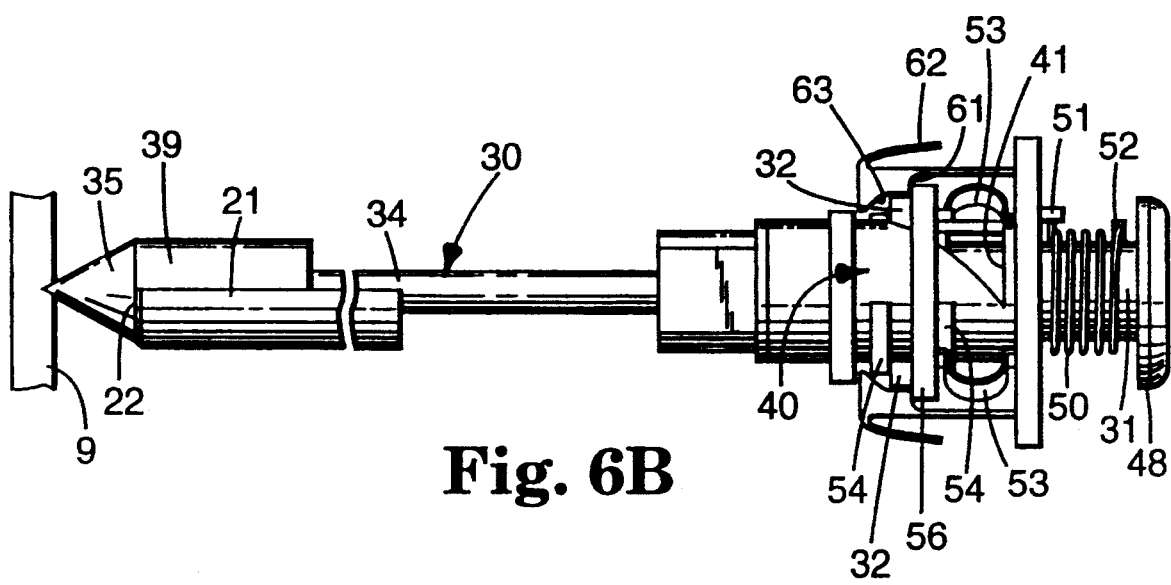
Figure 6C:
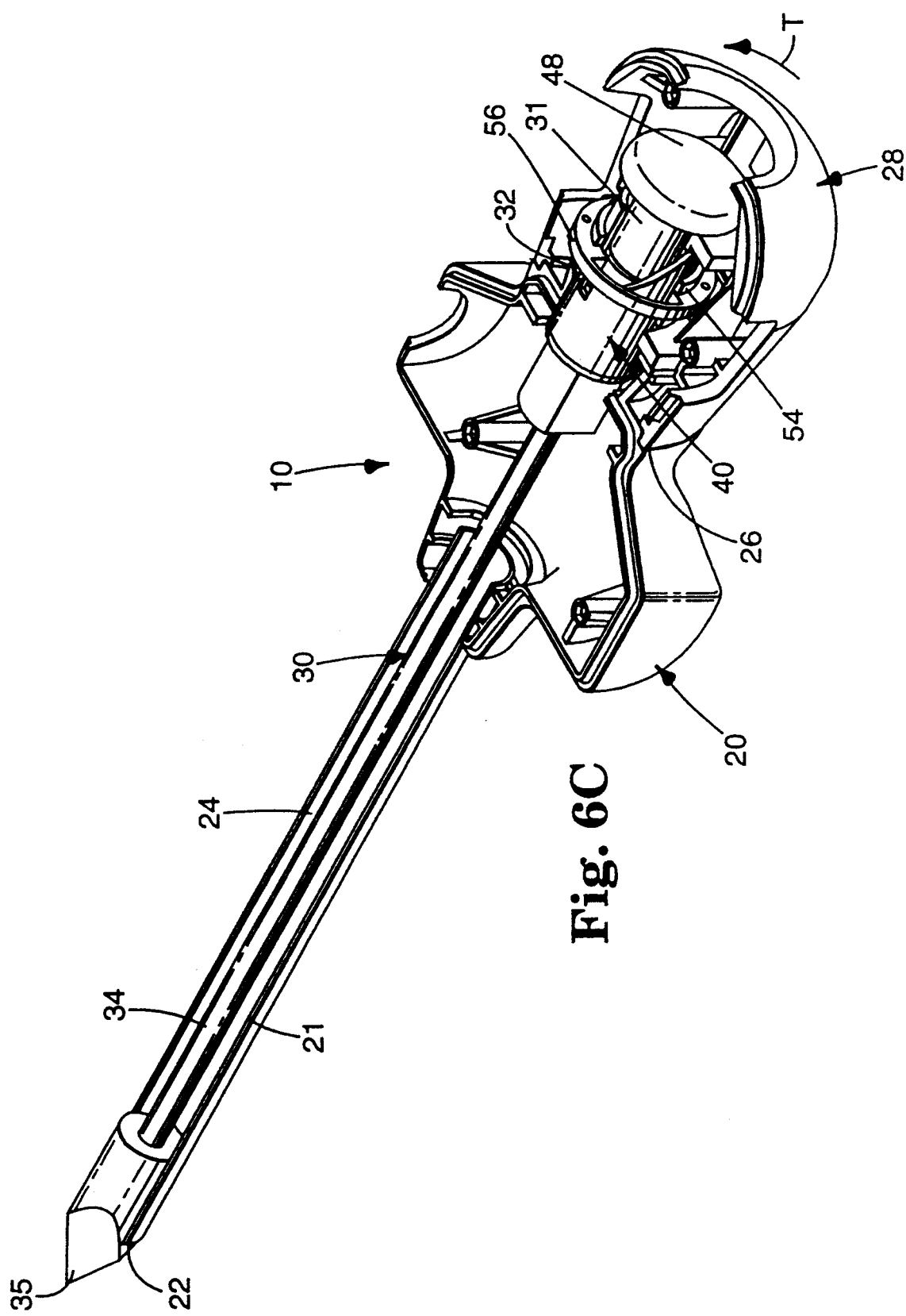

The cutting surfaces 35 may comprise any suitable geometry and are illustrated in FIGS. 2 and 3B, 4B, 5B and 6B as a generally conical shape terminating in a sharp point, and in FIGS. 3C, 4C and 6C as the intersections of three generally planar surfaces. However, any suitable cutting surfaces may be used, including a hollow structure with cutting surfaces on its periphery, such as the cutting surfaces shown in U.S. patent application Ser. No. 07/808,152, to Banks et al.

The trocar 10 of the present invention preferably includes an obturator 30 having surfaces (e.g. 39) adapted to abut at least the distal end of the cannula lumen 24. Preferably, the trocar 10 is free of structure between the obturator 30 and the cannula 20 at the distal end of the cannula 20 when the trocar is placed in the cannula. Note FIG. 2 which illustrates surfaces 39 of the trocar 10 which abut the distal end of the cannula lumen 24. A trocar that is free of structure between the obturator 30 and the cannula 20 at the distal end of the cannula 20 affords the maximum size of an obturator (and its associated cutting surfaces) for a given size of cannula lumen 24. Additionally, such a trocar is believed to exhibit a beneficial profile for ease of insertion of the trocar/cannula assembly.

Alternatively, but not preferably, the trocar 10 may include a thin, generally cylindrical member (not shown) that is coaxially mounted about the obturator 30 and which extends from the housing 28 a length, such that, when the trocar 10 is assembled in the cannula 20, the distal end of the thin, cylindrical member generally abuts or is spaced slightly proximally or distally from the distal end 22 of the cannula. Preferably, the thickness of the walls of the thin, cylindrical member is minimized (e.g. less than about 0.1 to about 0.3 millimeters). The thin, cylindrical member is rigidly attached to the housing 28 so that it does not move relative to the housing 28 or cannula 20 as the cannula is inserted into the abdominal cavity. In this embodiment, when the obturator 30 is in the position shown in FIG. 2 and the trocar 10 is subsequently withdrawn from the cannula 20, the obturator 30 will be situated within the thin, cylindrical member (e.g. the thin cylindrical member will extend distally beyond the cutting surfaces of the obturator). The end of the thin, cylindrical member assists in protecting a user's digits from coming into contact with the sharp obturator after the trocar 10 is removed from the cannula 20.

Figure 10:
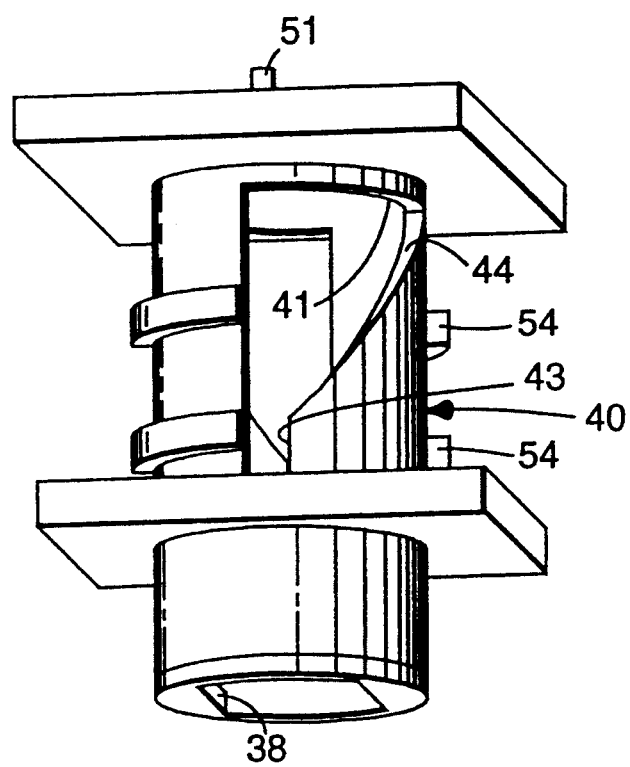
FIG. 10 is perspective view of a portion of a housing for use in a trocar according to the present invention.

The trocar 10 preferably includes a means for restricting rotation or angular displacement of the distal portion of the obturator relative to the housing 28 (and thus the cannula 20). As best seen in FIGS. 1 and 10, that means may comprise key surfaces 37 on the shaft 34 that are adapted to abut key way guide surfaces 38 formed on a portion of the housing 28. Abutment between the key surfaces 37 and the key way guide surfaces 38 prevents rotation of the shaft 34 of the obturator (the distal portion of the obturator) relative to the housing 28 (and thus the cannula 20), but allows the shaft 34 to move axially relative to the housing 28 when the obturator retracts or extends.

The trocar 10 also preferably includes a means mounting the pin 32 for angular movement relative to the distal portion of the obturator between an armed position (FIGS. 4A, 4B, 4C, 5A, 5B, 6A, 6B and 6C) and a release position (FIGS. 3A, 3B and 3C) that is angularly spaced from the armed position. That means may include the pin slot surfaces 36. Although the position of the pin 32 in FIG. 6A is axially spaced from the position of the pin 32 in FIG. 4A, as used in this application, the position of the pin 32 in both FIGS. 4A and 6A is referred to herein as being in the "armed" position as, in each Figure, the pin 32 is in generally the same angular position relative to the longitudinal axis A.

Figure 9:
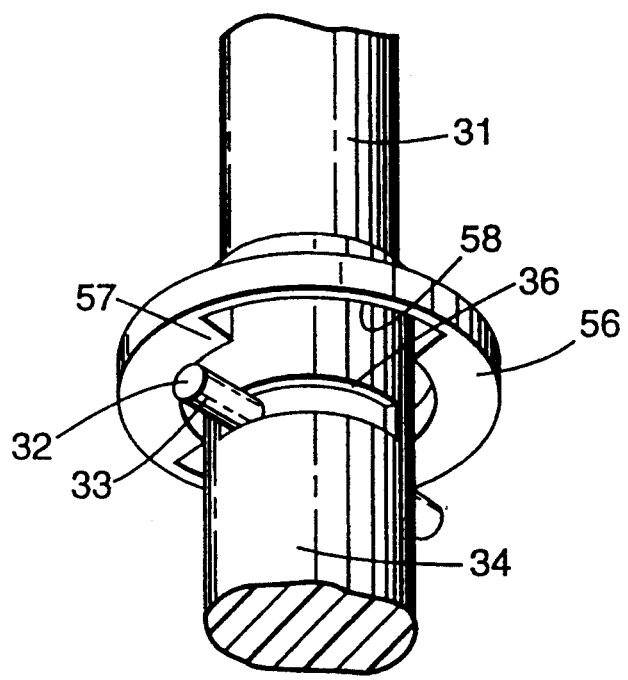
FIG. 9 is a perspective view of portions of an obturator for use in the trocar according to the present invention; with portions broken away to illustrate details.

As best seen in FIG. 9, when the trocar 30 is assembled, the pin 32 of the proximal portion 31 is received in the pin slot surfaces 36 of the distal portion of the obturator to allow the proximal portion of the obturator to rotate relative to the distal portion of the obturator. The pin slot surfaces 36 should be slightly wider than the diameter of the pin 32 to afford movement of the pin 32 between the armed and release positions.

The trocar 10 also preferably includes a button 48 associated with the obturator 30 that has surfaces adapted to be pressed by a user's digit (e.g. the user's thumb or finger). The button 48 is mounted to the proximal portion 31 of the obturator so that it can rotate relative to the proximal portion 31 of the obturator. For example, the undersurface of the button 48 may include an axially projecting shaft (not shown) that is adapted to be snap fit into a hole (see FIG. 1) in the proximal portion 31 of the obturator.

The trocar 10 includes a means mounting the obturator 30 for axial movement relative to the cannula 20 (and the housing 28 as well). That means may comprise an obturator sleeve or guide 40 mounted to the housing 28 so that the sleeve 40 does not move relative to the housing 28 (or cannula 20 when the trocar is inserted in the cannula). The guide 40 has guide surfaces adapted to abut the pin 32 of the proximal portion 31 of the obturator. The guide surfaces include proximal 41 and distal 42 end surfaces, ledge surfaces 43 and ramp or spiral surfaces 44.

When the pin 32 abuts the proximal end surface 41, the obturator 30 is in a retracted or proximalmost position relative to the cannula 20 (or the housing 28), and when the pin 32 abuts the distal end surface 42, the obturator is in a distalmost position relative to the cannula 20 (or housing 28). As explained in greater detail below, when the pin 32 abuts the ledge surface 43 and is in the position shown in FIGS. 5A and 5B, the obturator 30 is in an armed position, and when the pin 32 is in the position relative to the sleeve 40 shown in FIGS.

6A, 6B and 6C, the obturator 30 is in a tissue cutting position.

The trocar 10 also includes a retracting means for biasing the obturator 30 from the tissue cutting position (FIG. 6A, 6B and 6C) toward the retracted position (FIGS. 3A, 3B and 3C). The retracting means preferably comprises axial biasing means for axially biasing the obturator 30 from the tissue cutting position toward the retracted position, and angular biasing means for biasing the pin 32 from the armed (FIGS. 4A–4C, 5A–5B and 6A–6C) toward the release position (FIGS. 3A–3C).

The angular biasing means provides a torque $T_r$ about the axis A for moving the pin 32 from the armed toward the release position, and the axial biasing means provides an axial force ($F_r$) for moving the obturator 30 toward the retracted position. For example, the retracting means may comprise a torsion and compression coil spring 50 adapted to be coaxially mounted about the proximal portion 31 of the obturator. The spring 50 is in compression and also provides a torque about the axis A on the proximal portion 31 of the obturator in the direction T shown in FIGS. 1 and 2.

The spring 50 has a pair of ends. One of the spring's ends is operatively connected to (or abuts) a stud 51 which is attached to the sleeve 40 of the housing 28 and the other is operatively connected to a stud 52 on the proximal portion 31 of the obturator 30. While the retracting means has been illustrated as a single, coil spring 50, it should be noted that the retracting means may comprise any suitable type or number of springs so long as an angular and axial component of force are provided. For example, a pair of springs may be used comprising a leaf spring and a torsion spring. Other examples of suitable biasing means include compressed resilient members, gas/fluid springs and magnets.

The trocar 10 includes a clutch for retaining the obturator 30 in the tissue cutting position (FIGS. 6A through 6C) against the bias of the retracting means (e.g. spring 50) while the tissue 9 is being cut, and for releasing the obturator 30 to allow the retracting means to retract the obturator 30 from the tissue cutting position toward the retracted position (FIGS. 3A through 3C) after the trocar 10 has cut the tissue 9 sufficiently to afford passage of the cannula 20 into the abdominal cavity. Alternatively, the clutch may be described as a latching and mechanical sensing and releasing means.

The clutch comprises the proximal portion 31 of the obturator having a first, friction clutch surface 12, and the distal portion of the obturator 30 having a second, friction clutch surface 14. Since the keyway guide 38 holds the shaft 34 rotationally fixed relative to the housing 28 and cannula 20, the surface 12 may be referred to as a stationary clutch surface, and the surface 14 may be referred to as a movable clutch surface.

The resistance to rotation about the axis A provided by the first and second clutch surfaces 12 and 14 as the trocar is being inserted in the tissue 9 (See FIG. 6B) should be sufficient to overcome the torque T provided by spring 50. The resistance to rotation provided by the clutch will depend on numerous factors including, the friction coefficients of the first and second clutch surfaces 12 and 14, the size and shapes of the clutch surfaces, the minimum axial insertion force on the obturator (and thus the surfaces 12 and 14) and the tolerances and friction coefficients of the various components of the clutch (including those described below). The clutch should be designed to prevent rotation of the pin 32 from the armed toward the release position until the tissue 9 has been at least partially penetrated.

Figure 11:
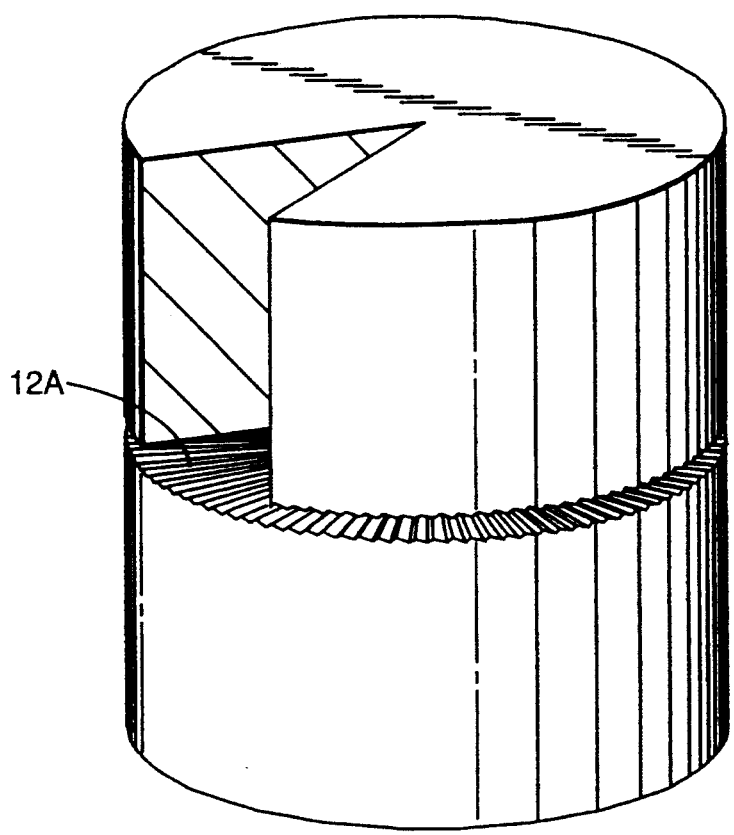
FIG. 11 is a perspective view illustrating a second species of clutch surfaces for use in the trocar according to the present invention, which favors rotation of a proximal portion of the obturator relative to a distal portion in one direction.
Figure 12:
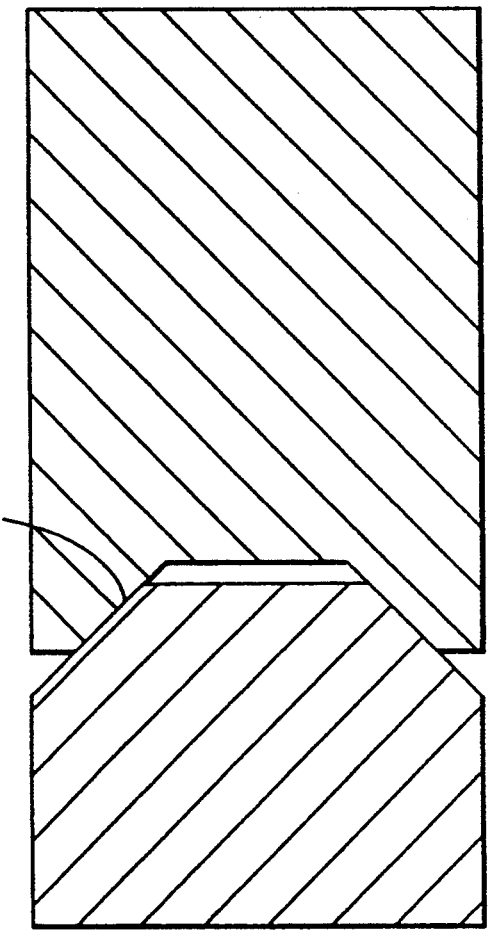
FIG. 12 is a sectional view of proximal and distal portions of a trocar having a third species of clutch surfaces, which illustrates frusto-conically shaped clutch surfaces.

While the clutch surfaces 12, 14 have been illustrated as generally circular, planar surfaces, it should be noted that the clutch surfaces may comprise any suitable shape, so long as the clutch surfaces afford angular (preferably rotational) movement of the proximal portion 31 of the obturator relative to the distal portion of the obturator 30. FIG. 12 illustrates a substantially frusto-conical clutch surface 12B. Other examples include a substantially conical shaped clutch surface, or any other surfaces that are symmetrical about the axis A. FIG. 11 illustrates a clutch surface 12A which favors rotation of the clutch surfaces in one direction relative to the axis A over the other. This may be beneficial in assisting the user in arming the trocar.

Since the clutch temporarily retains the obturator 30 in the tissue cutting position against the bias of spring 50, the clutch also preferably comprises an arming ring 56 having shoulder surfaces 57 adapted to abut the pin 32 as the obturator is advanced through the tissue 9 (FIG. 6A). The shoulder surfaces 57 restrict movement of the obturator 30 from each of the distalmost, armed and tissue cutting positions toward the retracted position. The arming ring 56 also includes surfaces defining an aperture 58 which are angularly spaced (relative to the axis A) from the shoulder surfaces 57 and which allow the pin 32 to pass when the obturator 30 moves between the retracted and distalmost positions.

A means such as arming ring stops 54 on the sleeve 40 mount the arming ring 56 for axial movement between a distal position (FIGS. 4A, 4B, 4C, 5A and 5B) and a proximal position (3A, 3B, 3C, 6A, 6B, 6C). The clutch also preferably includes an arming ring biasing means such as generally U-shaped springs 53 for providing an arming ring biasing force ($F_a$) that axially biases the arming ring 56 distally. Preferably, the arming ring biasing force ($F_a$) is at least ten times greater than the axial force ($F_r$) provided by the spring 50 to assist in preventing the premature firing of the trocar 10.

The U-shaped springs each have a pair of ends, one of which is operatively associated (e.g. attached) with the arming ring 56 and the other being operatively associated with the housing 28 (through engagement with base portions of the sleeve 40). Additionally, the clutch preferably comprises retaining means, such as leaf spring retainers for releasably retaining the arming ring 56 in the proximal position against the bias of U-shaped springs 53. The leaf spring retainers are movable relative to the housing 28 and arming ring 56 between an engaged position (FIGS. 3A, 3B, 3C, 6A, 6B, 6C) where engagement surfaces 61 engage the arming ring 56 to hold the arming ring 56 in the proximal position against the bias of springs 53, and a disengaged position (FIGS. 4A, 4B, 4C, 5A and 5B) which is spaced from the engaged position and allows the arming ring 56 to move toward the distal position.

The leaf spring retainers have a leaf spring 62 which is adapted to abut a portion of the housing 28 to bias the leaf spring retainer toward the engaged position, and cam follower surfaces 63 that are adapted to engage cam surfaces 33 on the pin 32 to move the leaf spring retainers from the engaged toward the disengaged position. This action is described in greater detail below.

The leaf spring retainers may comprise any suitable shape such as the shape shown in FIGS. 3A through 6C. Alternative, the leaf spring retainers may comprise the shape shown in FIGS. 7A through 7F, or any suitable shape or combination of springs and other elements. For example, the retaining means may comprise a torsion spring with a cam follower surface for cooperating with the shape of the cam surface on pin 32, and a retaining or engagement surface.

Any suitable materials may be used to construct the elements of the trocar and cannula according to the present invention. For example, medical grade plastics and metals may be used.

OPERATION

The operation of the trocar 10 will now be described with reference to FIGS. 1 through 10, and particularly to FIGS. 3A through 6C. Typically, the trocar will be transported in a transportation package in an assembled position, that is, the trocar 10 will be inserted into the lumen 24 of the cannula 10 with the elements of the trocar and cannula generally in the position shown in FIGS. 2 and 3A through 3C. Next, the trocar will be removed from the transportation package. In that position, the obturator 30 is in a retracted position and the cutting surfaces 35 are retracted within the distal end 22 of the cannula 20 so that sensitive or vulnerable items (such as the fingers D of medical personnel) are somewhat protected from contact with the sharp cutting surfaces 35.

Also, in the retracted position, the U-shaped springs 53 do not bias the obturator 30 distally. The engagement surfaces 61 of the leaf spring retainers engage the arming ring 56 and retain the ring 56 in the proximal position.

To initially prepare the trocar 10 to cut tissue in a laparoscopic procedure, a user may manually press (e.g. with the user's digit D) the button 48 distally relative to the housing 28 (and cannula 20). FIGS. 4A–4C illustrate the positions of some of the elements of the trocar 10 while a user is pressing on the button 48 and after the button 48 is moved to its distal limit.

FIGS. 7A–7D sequentially illustrate one example of the path that the pin 32 may follow when the pin moves from the position generally shown in FIGS. 3A–3C to the position shown in FIGS. 4A–4C. The pin 32 moves along the ramp surfaces 44 and through the aperture 58 of the arming ring 56. During that movement, engagement between the pin 32 and the ramp surfaces 44 of the sleeve 40 cause the pin 32 to be moved (cammed) angularly relative to the axis A from the release (FIG. 3A) toward to the armed (FIG. 4A) position. Also during that movement, the pin 32 is allowed to pass from a position spaced proximally relative to the arming ring 56 to a position spaced distally as the pin 32 passes through aperture 58 in the arming ring 56. Just after the pin 32 passes through aperture 58, the cam surfaces 33 on the pin 32 engage the cam follower surfaces 63 on the leaf spring retainers and move the leaf spring retainers from the engagement position to the disengaged position (FIG. 4A) thereby allowing the arming ring 56 to move from the proximal position to the distal position under the bias of U-shaped springs 53.

When a user releases pressure on the button member 48 after the button member 48 is moved to the position shown in FIGS. 4A, 4B and 4C, but prior to cutting tissue 9, the obturator 30 retracts slightly from the position shown in FIGS. 4A, 4B and 4C to the position shown in FIGS. 5A and 5B. The obturator 30 retracts due to the axial biasing force provided by spring 50, until it becomes operatively associated with the ring 56 and the bias provided by the U-shaped spring members 53.

Preferably, the axial biasing force provided by the spring 50 is less than the axial component of the arming ring biasing force provide by the U-shaped spring members 53. The arming ring 56 will remain in the distal position and the pin 32 will slightly retract due to the spring 50 until it contacts the shoulder 57 of the arming ring 56. Since the axial force provided by the spring members 53 is greater than the axial biasing force on the pin 32 provided by the spring 50, the pin 32 will not retract beyond the position shown in FIG. 5A.

This relationship may be described by the following equation:

$$F_i > F_a - F_r$$

wherein:
$F_i$ = the minimum axial insertion force on the obturator 30 as the obturator is advanced through the tissue 9;
$F_a$ = the axial force on the obturator 30 provided by the arming ring biasing force (e.g. provided by the springs 53) which biases the obturator 30 distally; and
$F_r$ = the axial force on the obturator provided by the axial biasing means (e.g. provided by the spring 50) which biases the obturator 30 proximally. Preferably, $F_a > 10$ times $F_r$, as a safety factor to restrict the chances that the obturator 30 will prematurely retract.

Figure 7A:
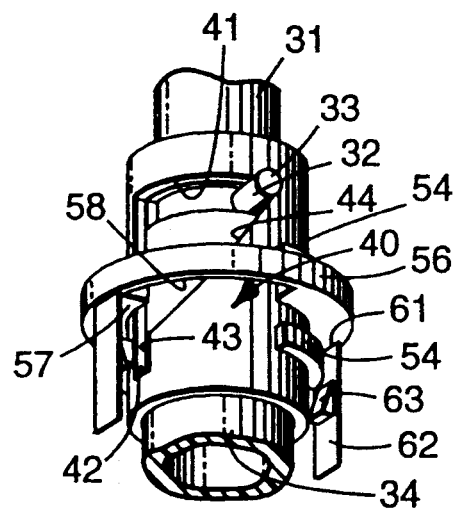
Figure 7B:
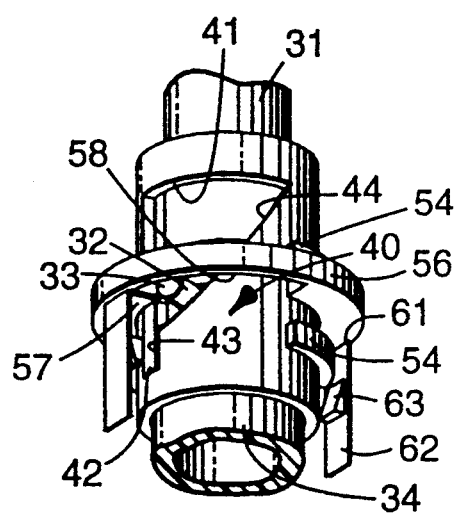
Figure 7C:
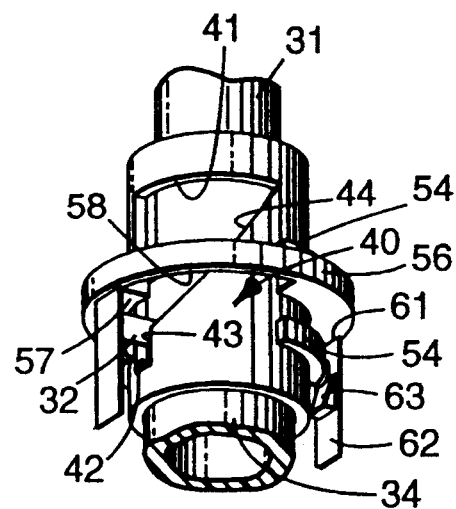
Figure 7D:
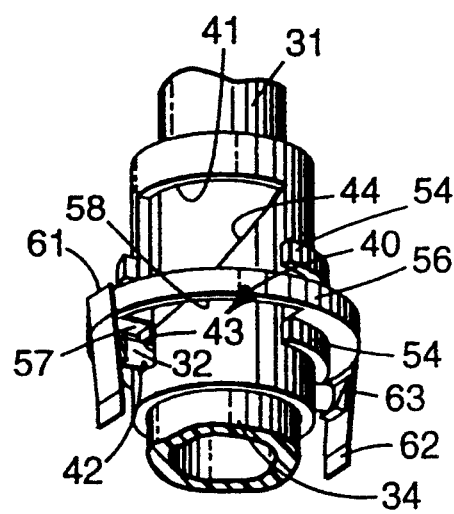
Figure 7E:
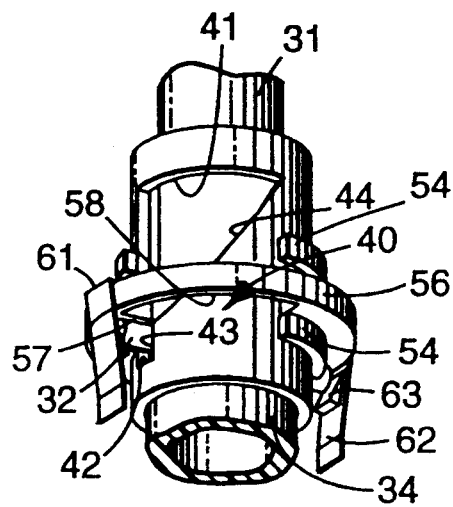

In the position shown in FIG. 5A, the pin 32 abuts the ledge surface 43 of the sleeve 40 (also see FIG. 7E). Abutment between the pin 32 and the ledge 43 blocks the pin 32 from rotating from the armed position toward the release position under the bias of the angular biasing means (the torque about axis A provided by the spring 50). The trocar 10 is now ready to be pressed against tissue 9.

Prior to the time the obturator 30 is pressed against the tissue 9, the U-shaped springs 53 bias the obturator 30 distally through abutment between the pin 32 and the shoulder surface 57 of the arming ring 56. The abutment between the shoulder surface 57 and the pin 32 resists movement of the obturator 30 toward the retracted position.

As the obturator 30 is pressed against the tissue 9, but prior to the complete penetration of the tissue 9, the elements of the trocar 10 will be in approximately the positions shown in FIGS. 6A through 6C. As the obturator 30 is initially pressed against the tissue 9, the arming ring 56 moves from the distal toward the proximal position where the engagement surfaces 61 of the leaf spring retainers engages the arming ring 56.

Figure 7F:
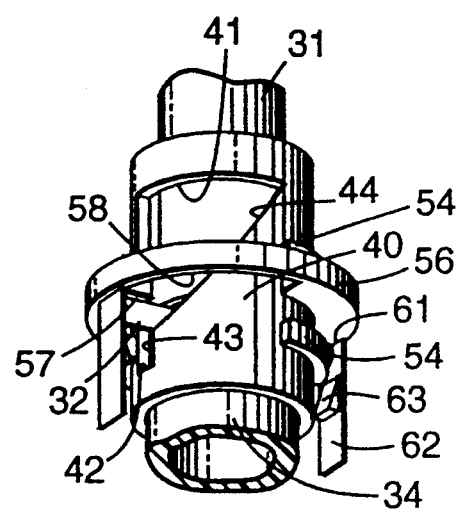

The obturator 30 is illustrated in the tissue cutting position in FIGS. 6A though 6C, and FIG. 7F. In the tissue cutting position, at least some of the cutting surfaces 35 of the obturator 30 project beyond the distal end 22 of the cannula 20.

As shown in FIG. 6A, as the obturator 30 is pressed through the tissue 9, the pin 32 is moved proximally off ledge surface 43 so that the ledge surface 43 no longer prevents the proximal portion 31 of the obturator 30 from rotating about the axis A relative to the distal portion of the obturator 30. However, when the obturator 30 is pressed against the tissue 9, the second, friction clutch surface 14 frictionally engages the first, friction clutch surface 12 and provides a first resistance to angular (e.g. rotational) movement between the proximal 31 and distal portions of the obturator 30 from the armed toward the release position. This first resistance to angular motion between the proximal 31 and distal portions of the obturator is greater than the torque about the axis A provided by the spring 50. Thus, as the trocar is being initially pressed against the tissue 9, the obturator 30 will not retract because the pin 32 will still abut the shoulder surface 57 of the ring 56.

When the tissue 9 is at least partially penetrated (preferably completely penetrated) or when the distal end 22 of the cannula 20 is generally adjacent the body cavity, the clutch automatically releases the obturator 30 to allow the spring 50 to retract the obturator 30 from the tissue cutting position toward the retracted position. When the tissue 9 is penetrated, the resistance to angular (e.g. rotational) movement between the proximal 31 and distal portions of the obturator 30 is less than the torque provided by the spring 50, due to the absence or reduction of drag on the obturator 30 (and the attendant reduction in the force that presses the clutch surfaces 12 and 14 together) that was previously provided by engagement with the tissue 9. Thus, the proximal portion 31 of the obturator 30 rotates from the armed toward the release position.

After the pin 32 rotates about axis A from the armed toward the release position, the pin 32 will clear the shoulder surface 57 of the arming ring 56, and the retracting means (spring 50) may then retract the obturator 30 from the tissue cutting position (see FIG. 7F) to the retracted position (see FIG. 7A).

Figure 8:
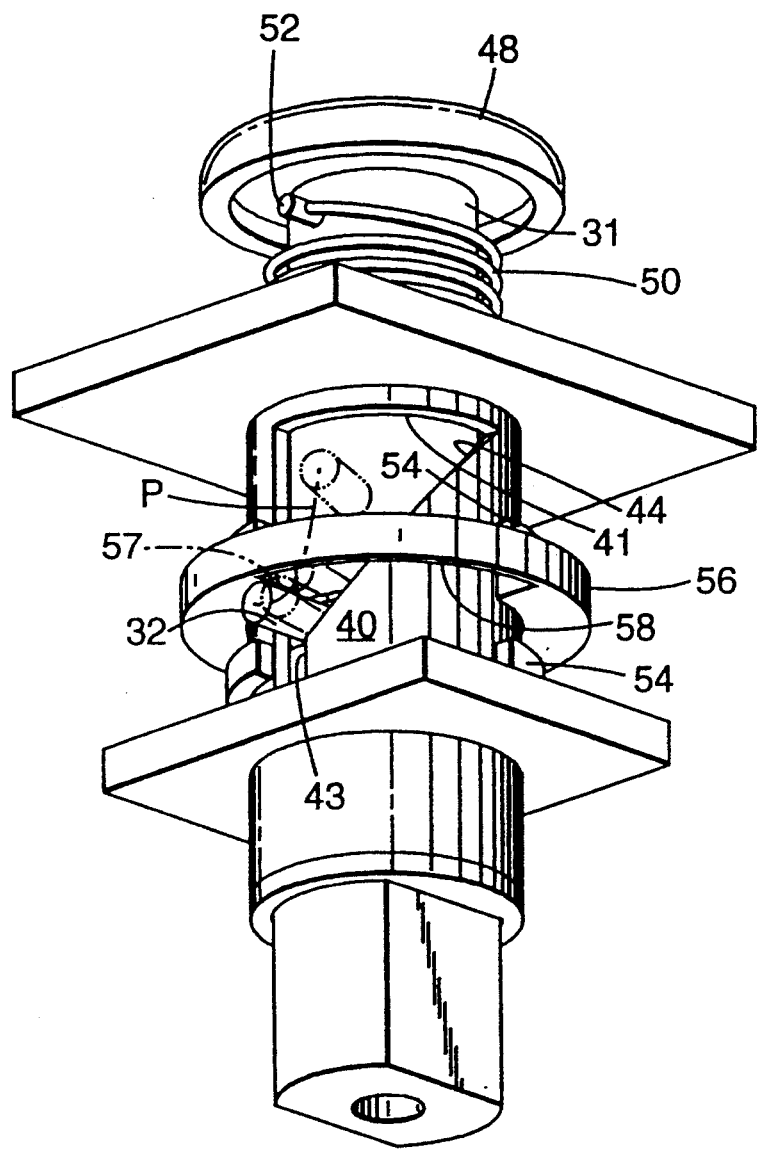
FIG. 8 is a perspective view of elements of a trocar according to the present invention which sequentially illustrates the position of a pin of the trocar just after the tissue is penetrated and as the trocar retracts from the position shown in FIGS. 6A through 6C toward the position shown in FIGS. 3A through 3C with dashed lines, and which illustrates one example of a path that the pin may follow.

FIG. 8 illustrates elements of the trocar 10 and four discrete positions of the pin 32 as it moves along one example of a path P from the armed toward the release position. As shown in FIG. 8, the path P is the path of the axis of the pin 32 as it moves from the armed position toward the release position. Preferably, the clutch affords movement of the obturator 30 from the tissue cutting position toward the retracted position along a path P that is completely free of distal movement of the obturator 30 relative to the cannula 20. However, the phrase "substantially free" is used herein as a recognition that when the clutch surfaces 12 and 14 initially begin to rotate relative to each other, there may be a slight, almost negligible distal movement of the obturator 30 relative to the cannula 20 which would depend on a number of factors including the spring constant of the spring 50 and the types of surfaces used for the friction clutch surfaces 12, 14. Preferably, there is no such distal movement of the obturator 30 relative to the cannula 20, and, in the event that there is any, it should be less than about 0.5 millimeters and more preferably less than about 0.2 millimeters. However, it is believed that it is possible to construct the friction clutch surfaces 12, 14 such that there is no distal movement of the obturator 30 relative to the cannula 20 as the obturator 30 penetrates into the body cavity.

The present invention has now been described with reference to several embodiments thereof. It will be apparent to those skilled in the art that many changes or additions can be made in the embodiments described without departing from the scope of the present invention. For example, optionally, but not preferably, the clutch and retracting means may be located in a distal portion of the obturator. Thus, the scope of the present invention should not be limited to the structures described in this application, but only by structures described by the language of the claims and the equivalents of those structures.

What is claimed is:

1. A trocar for placement in the lumen of a cannula to facilitate inserting the cannula through the wall of a body cavity, the trocar comprising:

a handle, an obturator having a proximal portion and a distal portion with a cutting surface for piercing the wall of the body cavity, and an axis, means mounting said proximal and distal portions for relative angular movement about the axis of the obturator, means for retracting said obturator proximally relative to the cannula as the proximal and distal portions move angularly relative to each other after the cutting surface has at least partially penetrated through the wall of the body cavity, wherein said retracting means comprises axial biasing means for axially biasing said obturator proximally toward a retracted position, and angular biasing means for angularly biasing said proximal portion of the obturator relative to the distal portion.

2. A trocar according to claim 1 wherein: the proximal portion of the obturator rotates relative to the distal portion after the cutting surface penetrates through the tissue defining the body cavity, and wherein the obturator retracts proximally upon the rotation of the proximal portion relative to the distal portion of the obturator.

3. A trocar according to claim 1 wherein the retracting means retracts the obturator along a path that is substantially free of distal movement of the obturator relative to the cannula.

4. A trocar according to claim 1 wherein the retracting means retracts the obturator along a path that is free of distal movement of the obturator relative to the cannula.

5. A trocar according to claim 1 wherein the cannula has a distal end, and when the retracting means retracts the obturator, the cutting surface is retracted within the distal end of the cannula.

6. A trocar for facilitating insertion of a cannula through tissue defining a body cavity, such as the abdominal wall of a patient, the cannula having a lumen terminating in a distal end, said trocar comprising:

a housing, an obturator extending from said housing, said obturator comprising:

a shaft for placement in the lumen of the cannula and cutting surfaces for cutting the tissue, said obturator is elongate and has a longitudinal axis, means mounting the obturator for movement between a tissue cutting position with at least some of the cutting surfaces of the obturator projecting beyond the distal end of the cannula, and a retracted position, and means mounting at least a portion of the obturator for angular movement about said longitudinal axis, retracting means for biasing the obturator from the tissue cutting position toward the retracted position, a clutch for retaining the obturator in the tissue cutting position against the bias of said retracting means while the tissue is being cut, and for releasing the obturator to allow the retracting means to retract the obturator from the tissue cutting position toward the retracted position after the trocar has at least partially penetrated the tissue, the clutch including angular biasing means for biasing at least a portion of the obturator and about said longitudinal axis, said retracting means comprising axial biasing means for axially biasing said obturator from said tissue cutting position toward said retracted position.

7. A trocar according to claim 6 wherein said clutch affords movement of the obturator from the tissue cutting position toward the retracted position along a path that is substantially free of distal movement of the obturator relative to the cannula.

8. A trocar according to claim 6 wherein when the obturator is in the retracted position, the cutting surfaces are retracted within the distal end of the cannula.

9. A trocar according to claim 6 wherein the clutch automatically releases the obturator to allow the retracting means to retract the obturator from the tissue cutting position toward the retracted position after the tissue has been at least partially penetrated.

10. A trocar according to claim 6 wherein:

said obturator's longitudinal axis defines angular displacements, said obturator comprises a proximal portion having a pin, and a distal portion, wherein said trocar includes means mounting said pin for angular movement relative to said distal portion of said obturator between an armed position relative to the longitudinal axis and a release position that is angularly spaced from said armed position, and wherein said retracting means retracts the obturator from the tissue cutting position to the retracted position after the pin moves from the armed position toward the release position.

11. A trocar for facilitating insertion of a cannula through tissue defining a body cavity, such as the abdominal wall of a patient, the cannula having a lumen terminating in a distal end, said trocar comprising:

a housing, an obturator extending from said housing, said obturator comprising:

a shaft for placement in the lumen of the cannula and cutting surfaces for cutting the tissue, means mounting the obturator for movement between a tissue cutting position with at least some of the cutting surfaces of the obturator projecting beyond the distal end of the cannula, and a retracted position, retracting means for biasing the obturator from the tissue cutting position toward the retracted position, a clutch for retaining the obturator in the tissue cutting position against the bias of said retracting means while the tissue is being cut, and for releasing the obturator to allow the retracting means to retract the obturator from the tissue cutting position toward the retracted position after the trocar has at least partially penetrated the tissue, said obturator is elongate and has a longitudinal axis defining angular displacements, said obturator comprises a proximal portion having a pin, and a distal portion, wherein said trocar includes means mounting said pin for angular movement relative to said distal portion of said obturator between an armed position relative to the longitudinal axis and a release position that is angularly spaced from said armed position, wherein said retracting means retracts the obturator from the tissue cutting position to the retracted position after the pin moves from the armed position toward the release position, wherein:

said retracting means comprises axial biasing means for axially biasing said obturator from said tissue cutting position toward said retracted position, and angular biasing means for biasing said pin toward said release position.

12. A trocar according to claim 11 wherein:

said angular biasing means provides a torque for angularly moving the pin about the longitudinal axis from the armed toward the release position, and said axial biasing means provides an axial force for moving the obturator toward the retracted position.

13. A trocar according to claim 12 wherein:

said clutch comprises said proximal portion of said obturator having a first friction clutch surface, and said distal portion of said obturator having a second friction clutch surface, wherein when said obturator is pressed against the tissue, said second, friction clutch surface frictionally engages the first friction clutch surface and contributes to a first resistance to angular movement between said proximal and distal portions of said obturator from said armed toward said release position, and wherein when the tissue has been at least partially penetrated by said obturator, resistance to angular movement between said proximal and distal portions of said obturator is less than said torque and the proximal portion of said obturator is allowed to move angularly from said armed toward said release position.

14. A trocar for facilitating insertion of a cannula through tissue defining a body cavity, such as the abdominal wall of a patient, the cannula having a lumen terminating in a distal end, said trocar comprising:

a housing, an obturator extending from said housing, said obturator comprising:

a shaft for placement in the lumen of the cannula and cutting surfaces for cutting the tissue, means mounting the obturator for movement between a tissue cutting position with at least some of the cutting surfaces of the obturator projecting beyond the distal end of the cannula, and a retracted position, retracting means for biasing the obturator from the tissue cutting position toward the retracted position, a clutch for retaining the obturator in the tissue cutting position against the bias of said retracting means while the tissue is being cut, and for releasing the obturator to allow the retracting means to retract the obturator from the tissue cutting position toward the retracted position after the trocar has at least partially penetrated the tissue, said obturator is elongate and has a longitudinal axis defining displacements, said obturator comprises a proximal portion having a pin, and a distal portion, wherein said trocar includes means mounting said pin for angular movement relative to said distal portion of said obturator between an armed position relative to the longitudinal axis and a release position that is angularly spaced from said armed position, wherein said retracting means retracts the obturator from the tissue cutting position to the retracted position after the pin moves from the armed position toward the release position, wherein said means mounting said pin for angular movement comprises said housing having guide surfaces including a ledge surface adapted to abut the pin to retain the pin in the armed position prior to the obturator being advanced against the tissue, and said clutch comprises an arming ring having a shoulder surface adapted to abut the pin as the obturator is advanced through the tissue to restrict movement of the obturator from the tissue cutting position to the retracted position, and surfaces defining an aperture which are angularly spaced from said shoulder surface and which allow the pin to pass when the obturator moves from the tissue cutting position toward the retracted position.

15. A trocar according to claim 14 wherein said clutch comprises:

means mounting the arming ring for axial movement between a distal position and a proximal position, arming ring biasing means for providing an arming ring biasing force for biasing the arming ring distally, retaining means for releasably retaining the arming ring in the proximal position against the bias of said arming ring biasing means, wherein, prior to pressing the obturator against the tissue, the arming ring biasing means biases the obturator distally through abutment between the pin and the shoulder surface of the arming ring, and the abutment between the shoulder surface of the arming ring and the pin resists movement of said obturator to said retracted position, and as the obturator is pressed against the tissue, the arming ring moves from said distal position toward the proximal position where the retaining means engages the arming ring to retain the arming ring in the proximal position.

16. A trocar according to claim 15 wherein: the retracting means is designed such that:

$$F_i > F_a - F_r;$$

wherein:
$F_i$ = the minimum axial insertion force on the obturator as the obturator is advanced through the tissue;
$F_a$ = the axial force on the obturator provided by the arming ring biasing force which biases the obturator distally; and
$F_r$ = the axial force on the obturator provided by the axial biasing means which biases the obturator proximally.

17. A trocar according to claim 16 wherein: the retracting means is preferably designed such that:

$$F_a > 10(F_r),$$

to restrict premature retraction of the obturator.

18. A trocar for facilitating insertion of a cannula through tissue defining a body cavity, and adapted to be placed at least partially in the cannula, the cannula having a lumen terminating in a distal end, said trocar comprising:

a handle, an elongate obturator extending from said handle having a longitudinal axis, said obturator comprising:

a shaft for placement in the lumen of the cannula and cutting surfaces for cutting the tissue defining the body cavity, means mounting the obturator for movement between a tissue cutting position with at least some of the cutting surfaces of the obturator projecting beyond the distal end of the cannula, and a retracted position, and means mounting at least a portion of the obturator for angular movement about said longitudinal axis, said obturator having surfaces adapted to abut at least the distal end of the cannula lumen, wherein the trocar is free of structure between the obturator and the cannula at the distal end of the cannula when the trocar is placed in the cannula, retracting means for moving the obturator from said tissue cutting position toward said retracted position including axial biasing means for biasing the obturator toward said retracted position, latch means for releasably holding the obturator in the tissue cutting position against the bias of said biasing means, mechanical sensing and releasing means for sensing when the tissue defining the body cavity has been penetrated and for releasing the latch means to allow the retracting means to retract the obturator from the tissue cutting position to the retracted position after the tissue defining the body cavity has been at least partially penetrated so that movement of the obturator from the tissue cutting position toward the retracted position is free of distal movement of the obturator relative to the cannula, and angular biasing means for biasing at least a portion of the obturator about said longitudinal axis, and wherein the axial biasing means biases the obturator from said tissue cutting position toward said retracted position.

19. A trocar according to claim 18 wherein said latch, mechanical sensing and releasing means comprise a clutch.

20. A trocar according to claim 19 wherein the clutch automatically releases the obturator to allow the retracting means to move the obturator from the tissue cutting position toward the retracted position after the tissue has been at least partially penetrated.

21. A trocar according to claim 19 wherein:

said obturator's longitudinal axis defines angular displacements, said obturator comprises a proximal portion having a pin, and a distal portion, wherein said trocar includes means mounting said pin for angular movement relative to said distal portion of said obturator between an armed position relative to the longitudinal axis and a release position that is angularly spaced from said armed position, and wherein said retracting means moves the obturator from the tissue cutting position to the retracted position after the pin moves about the longitudinal axis from the armed position toward the release position.

22. A trocar according to claim 18 wherein when the obturator is in the retracted position, the cutting surfaces are retracted within the distal end of the cannula.

23. A trocar for facilitating insertion of a cannula through tissue defining a body cavity, and adapted to be placed at least partially in the cannula, the cannula having a lumen terminating in a distal end, said trocar comprising:

a handle, an obturator extending from said handle, said obturator comprising:

a shaft for placement in the lumen of the cannula and cutting surfaces for cutting the tissue defining the body cavity, means mounting the obturator for movement between a tissue cutting position with at least some of the cutting surfaces of the obturator projecting beyond the distal end of the cannula, and a retracted position, said obturator having surfaces adapted to abut at least the distal end of the cannula lumen, wherein the trocar is free of structure between the obturator and the cannula at the distal end of the cannula when the trocar is placed in the cannula, retracting means for moving the obturator from said tissue cutting position toward said retracted position including biasing means for biasing the obturator toward said retracted position, latch means for releasably holding the obturator in the tissue cutting position against the biasing of said biasing means, mechanical sensing and releasing means for sensing when the tissue defining the body cavity has been penetrated and for releasing the latch means to allow the retracting means to retract the obturator from the tissue cutting position to the retracted position after the tissue defining the body cavity has been at least partially penetrated so that movement of the obturator from the tissue cutting position toward the retracted position is free of distal movement of the obturator relative to the cannula, said obturator is elongate and has a longitudinal axis defining angular displacements, said obturator comprises a proximal portion having a pin, and a distal portion, wherein said trocar includes means mounting said pin for angular movement relative to said distal portion of said obturator between an armed position relative to the longitudinal axis and a release position that is angularly spaced from said armed position, wherein said retracting means moves the obturator from the tissue cutting position to the retracted position after the pin moves about the longitudinal axis from the armed position toward the release position, and wherein:

said retracting means comprises axial biasing means for axially biasing said obturator from said tissue cutting position toward said retracted position, and angular biasing means for biasing said pin toward said release position.

24. A trocar according to claim 23 wherein:

said angular biasing means provides a torque for angularly moving the pin about the longitudinal axis from the armed position toward the release position, and said axial biasing means provides an axial force for moving the obturator toward the retracted position.

25. A trocar according to claim 24 wherein:

wherein said latch, mechanical sensing and releasing means comprise a clutch, said clutch comprises said proximal portion of said obturator having a first friction clutch surface, and said distal portion of said obturator having a second friction clutch surface, wherein when said obturator is pressed against the tissue, said second friction clutch surface frictionally engages the first friction clutch surface and contributes to a first resistance to angular movement between said proximal and distal portions of said obturator from said armed position toward said release position, and wherein when the tissue has been at least partially penetrated by said obturator, resistance to angular movement between said proximal and distal portions of said obturator is less than said torque and the proximal portion of said obturator is allowed to move angularly from said armed toward said release position.

26. A trocar for facilitating insertion of a cannula through tissue defining a body cavity, and adapted to be placed at least partially in the cannula, the cannula having a lumen terminating in a distal end, said trocar comprising:

a handle, an obturator extending from said handle, said obturator comprising:

a shaft for placement in the lumen of the cannula and cutting surfaces for cutting the tissue defining the body cavity, means mounting the obturator for movement between a tissue cutting position with at least some of the cutting surfaces of the obturator projecting beyond the distal end of the cannula, and a retracted position, said obturator having surfaces adapted to abut at least the distal end of the cannula lumen, wherein the trocar is free of structure between the obturator and the cannula at the distal end of the cannula when the trocar is placed in the cannula, retracting means for moving the obturator from said tissue cutting position toward said retracted position including biasing means for biasing the obturator toward said retracted position, latch means for releasably holding the obturator in the tissue cutting position against the bias of said biasing means, mechanical sensing and releasing means for sensing when the tissue defining the body cavity has been penetrated and for releasing the latch means to allow the retracting means to retract the obturator from the tissue cutting position to the retracted position after the tissue defining the body cavity has been at least partially penetrated so that movement of the obturator from the tissue cutting position toward the retracted position is free of distal movement of the obturator relative to the cannula, wherein said latch, mechanical sensing and releasing means comprise a clutch, said obturator is elongate and has a longitudinal axis defining angular displacements, said obturator comprises a proximal portion having a pin, and a distal portion, wherein said trocar includes means mounting said pin for angular movement relative to said distal portion of said obturator between an armed position relative to the longitudinal axis and a release position that is angularly spaced from said armed position, wherein said retracting means moves the obturator from the tissue cutting position to the retracted position after the pin moves about the longitudinal axis from the armed position toward the release position, wherein said means mounting said pin for angular movement comprises said handle having guide surfaces including a ledge surface adapted to abut the pin to retain the pin in the armed position prior to the obturator being advanced against the tissue, said clutch comprises an arming ring having a shoulder surface adapted to abut the pin as the obturator is advanced through the tissue to restrict movement of the obturator from the tissue cutting position to the retracted position, and surfaces defining an aperture which are angularly spaced from said shoulder surface and which allow the pin to pass when the obturator moves from the tissue cutting position toward the retracted position.

27. A trocar according to claim 26 wherein said clutch comprises:

means mounting the arming ring for axial movement between a distal position and a proximal position, arming ring biasing means for providing an arming ring biasing force for biasing the arming ring distally, retaining means for releasably retaining the arming ring in the proximal position against the bias of said arming ring biasing means, wherein, prior to pressing the obturator against the tissue, the arming ring biasing means biases the obturator distally through abutment between the pin and the shoulder surface of the arming ring, and the abutment between the shoulder surface of the arming ring and the pin resists movement of said obturator to said retracted position, and, as the obturator is pressed against the tissue, the arming ring moves from said distal position toward the proximal position where the retaining means engages the arming ring to retain the arming ring in the proximal position.

28. A trocar according to claim 27 wherein: the retracting means is designed such that:

$F_i > F_a - F_r$;

wherein:

$F_i$ = the minimum axial insertion force on the obturator as the obturator is advanced through the tissue;

$F_a$ = the axial force on the obturator provided by the arming ring biasing force which biases the obturator distally; and $F_r$ = the axial force on the obturator provided by the axial biasing means which biases the obturator proximally.

29. A trocar according to claim 28 wherein: the retracting means is preferably designed such that:

$F_a > 10(F_r)$, to restrict premature retraction of the obturator.

30. In combination, a cannula having a lumen terminating in a distal end, and a trocar for facilitating insertion of the cannula through tissue defining a body cavity, such as the abdominal wall of a patient, said trocar comprising:

a housing, an obturator extending from said housing, said obturator comprising:

a shaft for placement in the lumen of the cannula and cutting surfaces for cutting the tissue, said obturator is elongate and has a longitudinal axis, means mounting the obturator for movement between a tissue cutting position with at least some of the cutting surfaces of the obturator projecting beyond the distal end of the cannula, and a retracted position, and means mounting at least a portion of the obturator for angular movement about said longitudinal axis, retracting means for biasing the obturator from the tissue cutting position toward the retracted position, a clutch for retaining the obturator in the tissue cutting position against the bias of said retracting means while the tissue is being cut, and for releasing the obturator to allow the retracting means to retract the obturator from the tissue cutting position toward the retracted position after the trocar has cut tissue sufficiently to pass the cannula into the body cavity, the clutch including angular biasing means biasing at least a portion of the obturator about said longitudinal axis, said retracting means comprising axial biasing means for axially biasing said obturator from said tissue cutting position toward said retracted position.

31. A combination according to claim 30 wherein said clutch affords movement of the obturator from the tissue cutting position toward the retracted position along a path that is substantially free of distal movement of the obturator relative to the cannula.

32. A combination according to claim 30 wherein when the obturator is in the retracted position, the cutting surfaces are retracted within the distal end of the cannula.

33. A combination according to claim 30 wherein the clutch automatically releases the obturator to allow the retracting means to retract the obturator from the tissue cutting position toward the retracted position after the tissue has been at least partially penetrated.

34. A combination according to claim 30 wherein:

said obturator's longitudinal axis defines angular displacements, said obturator comprises a proximal portion having a pin, and a distal portion, wherein said trocar includes means mounting said pin for angular movement relative to said distal portion of said obturator between an armed position relative to the longitudinal axis and a release position that is angularly spaced from said armed position, and wherein said retracting means retracts the obturator from the tissue cutting position to the retracted position after the pin moves about the longitudinal axis from the armed toward the release position.

35. A combination according to claim 30 wherein said clutch is independent of said cannula.

36. In combination, a cannula having a lumen terminating in a distal end, and a trocar for facilitating insertion of the cannula through tissue defining a body cavity, such as the abdominal wall of a patient, said trocar comprising:

a housing, an obturator extending from said housing, said obturator comprising:

a shaft for placement in the lumen of the cannula and cutting surfaces for cutting the the tissue, means mounting the obturator for movement between a tissue cutting position with at least some of the cutting surfaces of the obturator projecting beyond the distal end of the cannula, and a retracted position, retracting means for biasing the obturator from the tissue cutting position toward the retracted position, a clutch for retaining the obturator in the tissue cutting position against the bias of said retracting means while the tissue is being cut, and for releasing the obturator to allow the retracting means to retract the obturator from the tissue cutting position toward the retracted position after the trocar has cut tissue sufficiently to pass the cannula into the body cavity, said obturator is elongate and has a longitudinal axis defining angular displacements, said obturator comprises a proximal portion having a pin, and a distal portion, wherein said trocar includes means mounting said pin for angular movement relative to said distal portion of said obturator between an armed position relative to the longitudinal axis and a release position that is angularly spaced from said armed position, wherein said retracting means retracts the obturator from the tissue cutting position to the retracted position after the pin moves about the longitudinal axis from the armed toward the release position, and wherein:

said retracting means comprises axial biasing means for axially biasing said obturator from said tissue cutting position toward said retracted position, and angular biasing means for biasing said pin toward said release position.

37. A combination according to claim 36 wherein:

said angular biasing means provides a torque for angularly moving the pin about the longitudinal axis from the armed toward the release position, and said axial biasing means provides an axial force for moving the obturator toward the retracted position.

38. A trocar according to claim 37 wherein:

said clutch comprises said proximal portion of said obturator having a first friction clutch surface, and said distal portion of said obturator having a second friction clutch surface, wherein when said obturator is pressed against the tissue said second, friction clutch surface frictionally engages the first friction clutch surface and contributes to a first resistance to angular movement between said proximal and distal portions of said obturator from said armed toward said release position, and wherein when the tissue has been at least partially penetrated by said obturator, resistance to angular movement between said proximal and distal portions of said obturator is less than said torque and the proximal portion of said obturator is allowed to move angularly about the longitudinal axis from said armed position toward said release position.

39. In combination, a cannula having a lumen terminating in a distal end, and a trocar for facilitating insertion of the cannula through tissue defining a body cavity, such as the abdominal wall of a patient, said trocar comprising:

a housing, an obturator extending from said housing, said obturator comprising:

a shaft for placement in the lumen of the cannula and cutting surfaces for cutting the tissue, means mounting the obturator for movement between a tissue cutting position with at least some of the cutting surfaces of the obturator projecting beyond the distal end of the cannula, and a retracted position, retracting means for biasing the obturator from the tissue cutting position toward the retracted position, a clutch for retaining the obturator in the tissue cutting position against the bias of said retracting means while the tissue is being cut, and for releasing the obturator to allow the retracting means to retract the obturator from the tissue cutting position toward the retracted position after the trocar has cut tissue sufficiently to pass the cannula into the body cavity, said obturator is elongate and has a longitudinal axis defining angular displacements, said obturator comprises a proximal portion having a pin, and a distal portion, wherein said trocar includes means mounting said pin for angular movement relative to said distal portion of said obturator between an armed position relative to the longitudinal axis and a release position that is angularly spaced from said armed position, wherein said retracting means retracts the obturator from the tissue cutting position to the retracted position after the pin moves about the longitudinal axis from the armed toward the release position, wherein said means mounting said pin for angular movement comprises said housing having guide surfaces including a ledge surface adapted to abut the pin to retain the pin in the armed position prior to the obturator being advanced against the tissue, and said clutch comprises an arming ring having a shoulder surface adapted to abut the pin as the obturator is advanced through the tissue to restrict movement of the obturator from the tissue cutting position to the retracted position, and surfaces defining an aperture which are angularly spaced from said shoulder surface and which allow the pin to pass when the obturator moves from the tissue cutting position toward the retracted position.

40. A trocar according to claim 39 wherein said clutch comprises:

means mounting the arming ring for axial movement between a distal position and a proximal position, arming ring biasing means for providing an arming ring biasing force for biasing the arming ring distally, retaining means for releasably retaining the arming ring in the proximal position against the bias of said arming ring biasing means, wherein, prior to pressing the obturator against the tissue, the arming ring biasing means biases the obturator distally through abutment between the pin and the shoulder surface of the arming ring, and the abutment between the shoulder surface of the arming ring and the pin resists movement of said obturator to said retracted position, and, as the obturator is pressed against the tissue, the arming ring moves from said distal position toward the proximal position where the retaining means engages the arming ring to retain the arming ring in the proximal position.

* * * * *

UNITED STATES PATENT AND TRADEMARK OFFICE
CERTIFICATE OF CORRECTION

PATENT NO.: 5,346,459

DATED: September 13, 1994

INVENTOR(S): John J. Allen

It is certified that error appears in the above-identified patent and that said Letters Patent is hereby corrected as shown below:

Col. 1, line 66, after "of" insert --the--.

Col. 5, line 30, after "obturator" insert --is--.

Col. 6, line 20, after "is" insert --a--.

Col. 9, line 58, "See" should be --see--.

Col. 16, line 32, delete the comma after "second".

Col. 17, line 4, after "defining" insert --angular--.

Col. 18, line 14, insert --and-- before "having".

Col. 19, line 39, "biasing" should be --bias--.

Col. 22, line 43, after "means" insert --for--.

Col. 24, line 6, after "tissue" insert a comma; delete the comma after "second".

Signed and Sealed this

Twenty-fifth Day of July, 1995

Attest:

BRUCE LEHMAN

Attesting Officer       Commissioner of Patents and Trademarks